United States Patent
Dorsey et al.

(10) Patent No.: US 9,273,287 B2
(45) Date of Patent: Mar. 1, 2016

(54) AVIAN REOVIRIDAE AND VACCINES THEREOF

(75) Inventors: Kristi Mae Dorsey, Shawnee, KS (US); John Konx Rosenberger, Lincoln University, PA (US); Sandra Cloud Rosenberger, Lincoln University, PA (US)

(73) Assignee: BIOMUNE COMPANY, Lenexa, KS (US)

( * ) Notice: Subject to any disclaimer, the term of this patent is extended or adjusted under 35 U.S.C. 154(b) by 925 days.

(21) Appl. No.: 13/000,492

(22) PCT Filed: Jun. 26, 2009

(86) PCT No.: PCT/US2009/048860
§ 371 (c)(1),
(2), (4) Date: Jan. 11, 2011

(87) PCT Pub. No.: WO2009/158618
PCT Pub. Date: Dec. 30, 2009

(65) Prior Publication Data
US 2011/0150928 A1  Jun. 23, 2011

Related U.S. Application Data

(60) Provisional application No. 61/076,102, filed on Jun. 26, 2008.

(51) Int. Cl.
| | | |
|---|---|---|
| *A61K 35/15* | (2015.01) | |
| *A61K 39/00* | (2006.01) | |
| *A61K 39/295* | (2006.01) | |

(Continued)

(52) U.S. Cl.
CPC . *C12N 7/00* (2013.01); *A61K 39/12* (2013.01); *A61K 39/15* (2013.01); *C07K 14/005* (2013.01); *G01N 33/569* (2013.01); *A61K 2039/525* (2013.01); *A61K 2039/5252* (2013.01); *A61K 2039/552* (2013.01); *A61K 2039/70* (2013.01); *C12N 2720/12221* (2013.01);

(Continued)

(58) Field of Classification Search
None
See application file for complete search history.

(56) References Cited

U.S. PATENT DOCUMENTS 4,795,635 A * 1/1989 Peleg et al. ............... 424/214.1
8,178,110 B2 * 5/2012 Sellers ...................... 424/215.1

FOREIGN PATENT DOCUMENTS

EP      1024189     8/2000
WO      WO 95/02417  1/1995

(Continued)

OTHER PUBLICATIONS

Wood et al., "Observations on the ability of avian reovirus vaccination of hens to protect their progeny against the effects of challenge with homologous and heterologous strains," Comp. Path. vol. 96 (1986).*

(Continued)

*Primary Examiner* — Benjamin P Blumel
*Assistant Examiner* — M. Franco Salvoza
(74) *Attorney, Agent, or Firm* — Saliwanchik, Lloyd & Eisenschenk

(57) ABSTRACT

This invention relates to novel unique strains avian reoviridae that were isolated from severe cases of Runting Stunting Syndrome. The present invention also relates to the isolation and uses of novel unique avian reoviridae, diagnostic assays using nucleotide or amino acid specific components of such viruses, such as the sequence encoding Sigma C capsid protein and to vaccines that protect birds from diseases caused by such viruses.

18 Claims, 14 Drawing Sheets

(51) Int. Cl.
| | |
|---|---|
| A61K 39/12 | (2006.01) |
| C12N 7/00 | (2006.01) |
| A61K 39/15 | (2006.01) |
| C07K 14/005 | (2006.01) |
| G01N 33/569 | (2006.01) |

(52) U.S. Cl.
CPC .............. C12N 2720/12222 (2013.01); C12N 2720/12234 (2013.01); C12N 2770/12034 (2013.01); G01N 2333/14 (2013.01)

(56) References Cited

FOREIGN PATENT DOCUMENTS

| | | |
|---|---|---|
| WO | WO 2004/032959 | 4/2004 |
| WO | WO 2008/076518 | 6/2008 |
| WO | WO 2008110004 A1 * | 9/2008 |

OTHER PUBLICATIONS

Duncan et al., "Extensive Sequence Divergence and Phylogenetic Relationships between the Fusogenic and Nonfusogenic Orthoreoviruses: A Species Proposal," Virology 260, pp. 316-328 (1999).*

Benavente et al., "Avian reovirus: Structure and biology," Virus Research 123: pp. 105-119 (2007).*

Lytle et al., "Predicted Inactivation of Viruses of Relevance to Biodefense by Solar Radiation," Journal of Virology, vol. 79, No. 22: 14244-14252 (2005).*

Hecht, "Gamma rays may have devastated life on Earth," New Scientist (Sep. 24, 2003).*

Rock et al., "Natural endogenous adjuvants," Springer Semin Immun 26: 231-246 (2005).*

Duffy et al., "Rates of evolutionary change in viruses: patterns and determinants," Nature Reviews Genetics, vol. 9: 267-276 (2008).*

Duncan, Roy, 1999, "Extensive Sequence Divergence and Phylogenetic Relationships Between the Fusogenic and Nonfusogenic Orthoreoviruses: A Species Proposal", Virology, vol. 260: 316-328.

Kawaguchi et al., 1987, "Establishment and Characterization of a Chicken Hepatocellular Carcinoma Cell Line, LHM", Cancer Research, vol. 47 (16): 4460-4464.

Li et al., 1996, "Production and Characterization of Monoclonal Antibodies Against Avian Reovirus Strain S1133", Avian Diseases, vol. 40(2): 349-357. (Abstract only).

Lin et al., 2006, "A Monoclonal Antibody-Based Competitive Enzyme-Linked Immunosorbent Assay for Detecting Antibody Production Against Avian Reovirus Protein SigmaA", Journal of Virological Methods, vol. 136 (1-2): 71-77.

Pantin-Jackwood et al., 2006, "Molecular Characterization and Typing of Chicken and Turkey Astroviruses Circulating in the United States: Implications for Diagnostics", Avian Diseases, vol. 50(3): 397-404.

Sellers, et al., 2007, "Molecular Characterization of Novel Avian Reoviruses Isolated from Chickens Experiencing a Runting Stunting Syndrome Reveal a Lack of Homogeneity with Current U.S. Isolates", Database EMBL Sequence Databse. (Abstract only).

Wood et al., 1986, "Observations on the Ability of Avian Reovirus Vaccination of Hens to Protect Their Progeny Against the Effect of Challenge with Homologous and Heteroloqus Strains", Journal of Comparative Pathology, vol. 96 (2): 125-129.

Yin et al., 2000, "Synthesis in *Escherichia coli* of Avian Reovirus Core Protein VarsigmaA and its dsRNA-binding Activity", Virology, vol. 266(1);33-41. (Abstract only).

PCT International Search Report, Mar. 9, 2010, for PCT International Application No. PCT/US2009/046860, filed Jun. 26, 2009.

PCT Written Opinion of the International Searching Authority, Mar. 9, 2010, for PCT International Application No. PCT/US2009/048860, filed Jun. 26, 2009.

* cited by examiner

FIGURE 1

SEQUENCE ID NO: 1

GTGGTCTAGCAACGAATCGTACTCAACTATCATCACTACTAACAAGCTCGAATTCCCCATGGCAACGATTTCTATCTTCAATG
ACTCCATTGACGGCGCCAGGTATTGTCTCAACACCTGAAGCACCCTATCCGGGCTCACTGTATCAAGAGTCCATGCTTCA
CAGTGCCACTGTCCCTGGAGTACTTGGTAATCGTTGATGCTTGGCGTTAATGTCTTCGGCTTTCATGGACTGACGAAG
GACTGTCAGGACTGGTGGCTGCTCAAGATCCTCCCGCCCCGTATCAGCCAGCCTCGTCTGCTTCAGTGGTCAGATCCCTC
AACTACCCCAGATGGGCGAACAGACGTCGTGAGTTACAATCAAAATACCCGCTTCTGCTTCGATCCACGCTGCTTTCTGCCAT
GCGAGCTGGTCCTGTTCTTTATGTTGAGACGTGGCCGAATATGATCTCAGGACGGCTAGCCGACTGGTTCATGTCCCAATATG
GCAACAATTTCGTTGACATGTGCCCAGTTGACACCGTTTTTTTGAACATGCCTGTCGAACCTGATGGGAATTACG

FIGURE 2

SEQUENCE ID NO: 2

```
GTGGTCTAGCAACGGATCGTACTCAACTATCATCACTACTAACAAGCTCGAATTCCCCATGGCAACGATTTCTATCTTCAATG
ACTCCATTGACGGGCGCCAGGTATTGTCTCAACACCTGAAGCACCCTATCCGGCTCACTGATGTATCAAGAGTCCATGCTTCA
CAGTGCCACTGTCCCTGGAGTACTTGGTAATCGTGATGCTTGGCGTACGTTTAATGTCTTCGGCTTTCATGGACTGACGAAG
GACTGTCAGGACTGGTGCTGCTCAAGATCCTCGCTCAAGACCTCTGCTATCAGCCCTCTGCTTCAGTGGTCAGATCTCCTC
AACTACCCCAGATGGGCGAACAGACGTCGTGAGTTACAATCAAAATACCCGCTTCTGATCCACGCTGTTCATGTCCCAATATG
GCGAGCTGGTCCTGTTCTTTATGTTGAGACGTGGCCCGAATATGATCTCAGGACGGCTAGCCGACTGGTTCATGTCCCAATATG
GCAACAATTTCGTTGACATGTGTGCCAGTTGACACAGTCTTGTTTGAACATGCCTTTGAACCTGATGGGAATTACG
```

FIGURE 4

SEQ ID NO: 3:

```
GCTTTCTCCGAACGCCGAAATGAGTTCGCGCAAAGTGGCTAGACGTCGTCATAAGGATGCTACTGATAATCTAAAGACACTAAGAACACTACTAAGTCTAAGCCATCTTCC
ACTGACGTTAAAGAATCGTAGAAAACGCCACAGACAAGAAAGTCACCGTCCCAAACCGCCTCCAAACCTACTGATTCTCCTCTACTGATGGGCTTCACAAAC
CTCAGTCGCTAAGCAGACGAATGATAATCGGTTAAGGAATCAGCTCCAAACCTACTGATCTAGTGATGGGAAAGATGCTATTACGAGAGACTGGGTCTGTTGAC
AAGACGCTAAAGCGACCGTAGCTGTAGTGTTCCAGCTGAAGACGCTACGATATCTTCAGCGGTGTGGCAAAAGCTATGATGGAGCAAAAGCAGCTTGTAGCTGGCCTTCGAAGCAACCGAAATC
AATGATGGGGCGTGTTAAGGTGTCTACTGTCTGCATGCCCCAGTTCGCTCATGGCCGTCATTCGCCGTCACAGCAAACTAAGCGGCTTGACGTGTCTCTGACAACCTTT
CGATTCATTGCTCTGTTGAAGAATTCATTCAGTGAGAATTGGGATTCCCGGTTATGTACATCTTTCGAACTGTCCCGATTGCCCGATTGCCCACTGTAGTGGATTCCCAATATGTTCAAGATGTATTCTATTCATGGTTAC
GTCAAGCTACAACATCACTACCCCCTTTCCACAGGCGACTGTCGTACAGGCTGTTTACGTACCAACATCCGATTGCTAAGTTGGATTCACCATCATCGCGGAAATGTG
ATCTTCGTCTTGCCCCCCCTACAGAGTAAGCGTAGGTCATTCTCGATGTGTGCACCTTACACTTAAACCTAGTACTCAATTTACCATGGATTTGACTGCCGCGGCTCCTAATCTTTCCGCGTCAACT
CCGTATTGTTCCAGAGATAAGGAGGGTAAATGGTTTCCGCTCAATTTCGCTGCGATATCGTGCACCTTCTGACCTATGCGCTCAGTGTCCTGACAACAGCGGACTCGCTAACTCTTTCCGTTCGTGAAATG
GTGATAGGATTGGCGTATTCGAAGTGATAACATTACTGCTGATGAACATTACCTCTGCTGACATTGGTACTCTCAGTCCTGTCCAGTGTCCTGGACCAGTGCCGATCGACCAGTGCCAGTACGTCCAGGCCGATTCTGTCTG
GCTGGCTTGTTACCCTCCGCTGTATTTCTGATGAAGGCAGCTCCTCCAATTGTTAATGCTAATCCGCCTAACGTATGTCGACGATGTGCGAGAGCACTGTCCGACAGCACTACAACCCAGAGCCCCCCT
CGTGCTAATCCTGTCAAACCTGGTCAAGCCTAAACCTGGCCTCTGATTTTTCGAACTGGTGTGCCGTTGTTATAAACGGTTGCGCGCCCCTAATGCTGTTCAGACATCTAAATGCTGTCTGAGGA
TCATATCCAAGTAGTGCGGTCCCGATCAAGCTTAAACCTGGCATTGAGACAGCGTATGTCGAGATGTCCTAAGCTTACCTCACGAGAGAATTGGCTCAGCAGAGATTTGGGCTGCGCAGAGATTGGGCTCGTCTAATTCACTCAGAGAGACAGATGCTGAGCAATTAACAATGCCAGAATTGGCGACGATTTGGGCGCAGCAGCAACTTCTTCAGACTG
CCTTTATGTGTCGCTACAGACCATGGTGGCTACTAGACAGAATCTGATCAGCAATCCGCAGACAGCAAATCGCAGACAGCAAATCAGAGAATCTAACAATCTAACAATCCACCATCCACCTGG
CCTCAGTGCTTCCTCCGATATCATTGGACGCCCAATCTTTCACTCCCCCTGATGTGCGCATCATGCGGAACGGTGTACCAGCGTATTACCAATCCGCGGTCCATGCGA
CGGTCACCTGACATCATTGGACGCTGGCTACTGCTTCAAGTCTTACACCTGCCATGCTGGTGGCCTTCACAGAGTACAGTACGCACCAAGCTATTCCGGCCCACATCGCATGCCCCAACTCGAATCAGGCGGTCCAGCCGCCAACTTGGCCACATCGCCGTCAGGCGGTCCAGCCGCCATGCATGCCCAACTTGGCCAGGCGGTCCAGCCGCCTAATCGGCGGTCCATGCGA
ATAATGAGTTGACGACGAATTTCAGGATTATCAAGTCTTACACCGTGGTCTTCGGCAGACGCTATCTCGGCAACGTGCAACAAATCTTGCCCAAACTGTCGTTAAATGTCATGACGT
CCAGGTAGCCGTTTGCTCGTTTGGATCGCTCTCAGCGCCTATCGTCACCCGTCCCTTAACAACGTGGTCTCTTCAGCCGCATGTTGCCTGCTAATGCTGCTCTCACAATTTGCTGCTCAGCTCTCACACTACTATGTCGCTCAGTACTG
ACCAGCGACAGGAGTTCCGATCCTCTAATGATGGTCTCTTTAACAACGTGGTCAACATGGCGACAGATTTTGCTCGAAGCGAACGAACTAGCCTTCTTCAGACTGAGCTGCACCGCGACGAATAGCCTTTGATCTCGATCAATCACTTTCCAGACTG
TGACATGCAATATCCGTGACCTGCCCTCGATCGCCCTCGAACTGGTGCGTCAGATTGGCTCAGATTAATGAGCGACAATGCTCAGATCTGACAACGCAACGTTTGGCTCAGACTATCAATTCCAGACTG
CCTTGACCTTCTGCTACGTGTTGCTTCAACCTTTCGGTCTTCAACCCTTAGCTCAGCGCCACATTGCTGAAGCGCCACATTGCTTGCTCTGACATCATTCT
TTCGTACCGACAGTACGGCCATCATGCGTCCATCTATGATCTGCTCTCATTATCAGCAGCCCCATGCTCATCAGATCGATGGTCCGGTTATGCCTCCAGCTTTGATGCAATATGGC
GGGACAACACATGACTGACTGCGTCAATCCCTTAGCTCCCGACATTCCCCATGCATCATGCGAATACAACTCTTCCATGAAATACAATCTCTGGATCTCGTAGCTCGGTA
ACTTCGGGTATGAATGGAGAGGAGATCTTGGTCATGGACGGATCGTCATTTGAAAGAGGACGTCTATATCAGATGAAGTTGGGCGTATCCCTACACGGCAGTAGTAGTAC
GTATTCCCAAGCTGTTTACATTGCTTGAGCAATGGATGTCCAAGGTGCCATGGTCACTCTCTAACAACTGCGCCACACTACTCATGCCACAGTTCCAATCAG
TGACGTTTTTACATTCGACTGCACTGTGTCACTGAAATGGATCCAAGGTGTCGCCAAGGTGTCACTAACAACTGCGCCACAGTCCCGGTTACTGTATTTGGGCCTGACACGTTACTATCTGGACGCCCTCAC
TGGCTACTCACTCGATCCAGGCCGATGGACTTATGCCGAACCATTAGAGCGGCGAGCTAGACGGCGAGCTATTAGAGCGGCGAGCTATCCCCGCGATGACTCCCCGCGATGGACTCTCGTTGGAGATTATTCATC
TACTGCCACTGTCACTACTTATGCCGATGGACTCCCCGCGATGGACTCTCGTTGGAGATTATTCATC
```

FIGURE 5

SEQ ID NO: 4

GCTTTCCTCACCATGCGTGTCAACGGGTTTGATGATGCTACTCTCTTACGCACAATCCATTTCGGGGGTTATTCCTATGACAATAAGTTATTTGAGCAAGCATCCG
CATCAATACGTGCTTTACCCCGATCACACGTTTACGCTCTGTTAGACGACGTTTAATTTCTCGTTTCATGCGTAATTCCAAATCGCATCTTCCACCACTCTGACCACTCT
GAGTATTTTACGTTGACGCGGTTAATAGAGTTAGGCGTAAACAGTTATTGATCCGTAAGATGTGTTCGTTCGTTATTTACGGGTCTCATCTCTCAATGA
GAGGTTACCGATTATGCCAGTTATCGGAAATATTTTGTCGAATGCTACGTGACGGCCTACTCTTTATCAGAGGATCCTCTGGTCTTGACACTACAGCTTCTGTGCCAAG
CTCGTCAGATTAAGGCTCCGCTTGATGGGTATAGCGTTATCAGCTCATCCCACCTCTTATGCTGAATTAGTCGAAACATTTTGTCGAAATTAGTCGAAACAGATCGCTCACCCTGGTTGTTGTACTTGACTCCGGTGTTGCTGGTT
ATTCATACAAATTAGCGTTAAGTCATCAGCTATCCCACCTCTTATGCTGAATTAGTCGAAACATTTGTGATCTTCAAAGGATCGCTCACCCTGGTTGTTGTACTTGACTCCGGTGTTGCTGGTT
CATGTCTCGTTAATGTCATCAGCTATCCCACCTCTTATGCTGAATTAGTCGAAACATTTGTGATCTTCAAAGGATCGCTCACCCTGGTTGTTGTACTTGACTCCGGTGTTGCTGGTT
TTCAAATGTTTTACAAGCTGCTCGTCACAGTCATTGATTGGTTGGAACCGCGTTCCAATTACGCGTTTCATGCTTCAGGGTGCGCGTAGGGTGACTTCAGATGACTTCACTCATTACTGTTCACTCACATGAAGTGCCATTCCA
GATGGCATCGTACCAGTCATTGATTGGTTGGAACCGCGTTCCAATTACGCGTTTCATGCTTCAGGGTGCGCGTAGGGTGACTTCAGATGACTTCACTCATTACTGTTCACTCACATGAAGTGCCATTCCA
TACGGAAGCAGCTGAGCAACTCGTCGTAAGATGGGATGCTTAGATGTGTATATTATTACACGTCAACCTACTGAGACTCTTCCTCGATCCTCTGAGACTGTTTAAAAGAGTATACCCAAGCTCCACTATTGAACGTGCCGCTTCCA
TCGTGCGTGACGCTGTCACCGCCATGCTGTCACCGCCATGTCTTTACGGTACCTTTCAGATCTTTATCAGGCTACTTCTCGCTCCCAATACGTGACATCCCGTTGGGTCTCGTGCAGCGCGTGAGAGATGTCCCCTTGATAAATTATCTGAGCCGTTCTA
CAATCGGACTCGTCACCGCCATGCTGTCACCGCCATGTCTTTACGGTACCTTTCAGATCTTTATCAGGCTACTTCTCGCTCCCAATACGTGACATCCCGTTGGGTCTCGTGCAGCGCGTGAGAGATGTCCCCTTGATAAATTATCTGAGCCGTTCTA
AGACAACCTCACACTTGGGATCCTTTATATCAGGCTACTTCTCGCTCCCAATACGTGACATCCCGTTGGGTCTCGTGCAGCGCGTGAGAGATGTCCCCTTGATAAATTATCTGAGCCGTTCTA
AGGTTGAGCTTCCTCAATATCCTGGGGTCAGTGTTAAGGTAGCCACTAAGATTTACCAAGGACGTCCAAGGACCATTATGCCTATGAATGTCGTCAACAACAGATTTCGGCGGCCCACACTCTCTCCGCTGA
GCTCCACTGTCAATGGGTCTGCGTAACCAAGTTCAGCGACGTCAAGGACCAGCAGCCGGTCATCGAGAAGGTAGTCGCGGCCATGATGCCACTGGCATGATGCAGCAGGGGCGTCGTTCGTTCTCCTGCTCTCAGGCGTTAATA
CTACATTAACTATCACATGAACCTATCGACAACATCAGGCAGCGGCCGTCATCGAGAAGGTAGTCGCGGCCATGATGCCACTGGCATGATGCAGCAGGGGCGTCGTTCGTTCTCCTGCTCTCAGGCGTTAATA
TCGACATTAAGGCATGTGACGCTTCTATTACGTTATCAGTATTTTCTTTCGGTTATTGTCGGCGGCCTATTCACGAGGGTCGCAGCAGGGCGTCGTGTCTCGTCCTCATTTATG
GGACATATTAAGGCATGTGACGCTTCTATTACGTTATCAGTATTTTCTTTCGGTTATTGTCGGCGGCCTATTCACGAGGGTCGCAGCAGGGCGTCGTGTCTCGTCCTCATTTATG
AGTTTTGAGTATCAAGTCACGGACCATTTCGCCAGGATTTCCTTTATCTGATGGCAAATATGTGTCATCCAGGTGCAAATATGTCAGGTGAAGAATAATGGCATAATGGCATGGCTAATCTCCTTCGTCCTTGATCGCCCCCTCGT
AATAACACGATGACGATGGGTCTAATGAGTTGGAATGCAAATGAGTCAGGCTGTCAGGTGAATGCAAATATCGACATATGGCATGGCATGGCATAATCTTATCCCTTATGCATGGCTATGCGTCGTCGTCGTCGTGCGTCGTGCGTGCGT
TGCCAGCGGCGACGATGTCAATGAGTCAGGCCACACGGACATGATGAATGCAAATGAGTCTTATCAACGGTTGTCGTATACCAACGTTTCTCAATATGGATCGTCCAATGCTATAATATACCGGGCTACACCCACCAACACGACCAACCTGT
TGGGGTGGAACTATCAGGAGGACAAACTGGAGATGTCTCTCATGTCTCATCTCTCCATCCTCCGGAAAATCTCTCCATGAATCGCGTGCGTGCATCATCCAGCCTGGAATGTATGCGTGCGTGATCCCTGGTCATTCTCGTTCCTC
AACGAGCCTCAGGAGACAAACTGGAGATGTCTCTCATGTCTCATCTCTCCATCCTCCGGAAAATCTCTCCATGAATCGCGTGCGTGCATCATCCAGCCTGGAATGTATGCGTGCGTGATCCCTGGTCATTCTCGTTCCTC
TATTGTTGGGCTCTTGGTCTTCGGTTCTGATCCTTGGCTATCCGGCTATTCCGATCTCTCCATGCGATCATAAACACCCCTGTTCAACCGCATAACCTGTAATGGCTTTTATTCAATTAGTAATATCAGGGTTACTATATGCGGCAATTCACCGTTCACCGACAACCT
TATCAGTGCTTCTTCCGTTCCGGTTCTGATCCTTGGCTATCCGGCTATTCCGATCTCTCCATGCGATCATAAACACCCCTGTTCAACCGCATAACCTGTAATGGCTTTTATTCAATTAGTAATATCAGGGTTACTATATGCGGCAATTCACCGTTCACCGACAACCT
CTCCCCGGTCGACGGTCATGGAGATCCCGATTCGGTGCTACACGGAGAAATCCGACCAATGAGTCGGTGCGTAGAGCTCTAGAGCGTCAAGGCCTTTGTCGAAGGCTCTAGAGGCTTCAAGGTGCTTCAAGGTGCTGAGTGCTCAAGGCGTATATCAATGAAGCCGCAATGAGACCGAGTGCTCAAGGTACTTGGCCG
TGATCGAGCAGAAATTGGTTGCGTACACGGAGAAATCCGACCAATGAGTCGGTGCGTAGAGCTCTAGAGCGTCAAGGCCTTTGTCGAAGGCTCTAGAGGCTTCAAGGTGCTTCAAGGTGCTGAGTGCTCAAGGCGTATATCAATGAAGCCGCAATGAGACCGAGTGCTCAAGGTACTTGGCCG
TAGAAATCAGGCCATGGATCGTCCTGTTATCGCAAGACGTCGGACATATCGCGGACATATCCGGTCTTCTAAATATGGAATACTTACTTGAGAGTGACTTGGACTTGTCCGAA
CCAATGACCACGCTGTGATCCCCGTGTCCTGTCGTGTCCCTCTGTGTGCTCGGTGTATATCCGTCGAATAGCGAGCCGTTCTTAAAATTGTACTCGTGCCGATGATGCAATGAC
ACGTAATATATTTCAGTAATACTTATTCATTCACGTAATCCGGTCTCGATGTCTGATGTGTCGATCGTGCTCTTTTGAGGTTGCGTGCACTCAATGCCTATG
ACGTGGTTGTACTCTCCAGCTCGTGATGATCGTCCCAGTGATCATGGACTCGTTAGGTAGGTTTATCCGAAGCCGAAGCGGCCAAGCGGCAGTCGAATCTTAGCTCGATGTGCAGTTAGCGAGAGTT
GTCATCTGTCTATCCCTGACTCTAATGAGATCGTGATGATGACTACTGGAAATATCCGCCAAGCCGCATGCTGCTGCCGATACTCGGTCATACTCGGTCATCTACC
GTCCGGTGTCCCATGGGCACGTGGAGATGTCCAGTCCAGTTCTTAGGTGCGGGATACTCGCAGTTCTTAGGGTGCGGGGATGCGTCTATGACCGGGTTGTCGGGATACTCCAGTTCTTAGGGTGCGGGATGCGTGAAACGAGGAGGCTCGAGGAATTACTCATC
TGGCATCGTCATTAAGCACAGTTCCGCCGGTGGATGCCGTGCGTGAAACGAGGAGGCTCGAGGAATTACTCATC

FIGURE 6

SEQ ID NO: 5

```
GCTTTCCACCATGGCTCTCAGATTAGAGGCCTTCGGTTGTCAACGACGCTCTCAGCTCCTCCTTCACGAAAGACTTTGACTTCACATACATACGATGAGCTAATATCTGC
GTTGAAGCTAACTACCAAACCATGGCGACCACTTAAGTCTAGGGATCGGAATTCCATCACCGCGGTGCAACTATTATTCCCCCATCAATGATATATCGAACCAATGTTCA
TACTGGAGAAAGACATGAGCTATGAGAGATTTGAGTCTTGGTTATCTCCGGCCTTGGCGGATCCATTCAGCTTTACGGCGTTACCCATTGCGTCTCACCATGGG
CGACTGGTTAATCCATTGCTTCCAATGCCATGCCATCTCGATCATCGTGTAGATCATCGCGTTGTCTATGGGGCTCGTATGCGTGCTATGGGCGTGCTATGGGCGTGCTATGCTGTGAATAATCGGCTCATTCATTCATATTGTCAACTATCGTGTTATCATTTCTCCT
CATTCTGGATGTCGGACTTTCGTTGTTTCAAAGCAACTCATGCGTTGCTATGGGCCTCGTATGGGCTCGTATGCTGCTGCTGCTGCTGCGTCCCTGTGCGATCATCTCCAATTCT
ACTCCTCTTATTCATTTCGATCGCCATGCCCATCATTAGCTGCGACCTGTAATGCTCTGAATACTCGCACCTGTACTACCATTCGTCCCCTTTCTTCG
CTTGCTCGAGTCTTTGTATTCAACAATCCTCTATTTGCGCTCCTAAGCGCTGGTTAATGCGTCCAGCTACAGCGAATCACCCGGATTGCGCGACTGTAGCC
GCTATTTAGCCAGGCTGATTGATTCTTCGAAGGACATTACTACCATTCGGGAACCCTATTGGTCCAGTCGTCGTGACACGCTATCGGTTGATGCCTATAGTGGTGAGAA
CGCTAACTTTATCCGGCGCTTACCCTGCTCTTCTGGAACCTGATTGGCTATGACTCCTTATCTAAAGCCACGACGCTTCGCGACTTGTTGACCGGTTCGCTCGGTCTGGTCTGTCCAGCTTATTCGTCTTTCG
CCTCTTCTACAATCCTGATTTGGCTATGGCTATGAATGGAATTTGCTGAAGACATGCTTTGAACGATCAGATCGATCAGAGCGCCTATTCCCACTCCCGAAGACCATGG
TGCGCCTGGAAGACAGATCTTTGCTGAAGACACGCGATAATCAGCGCCATCGTGATCAAGCCTTTATCTAAATGGGTCACTTCCGGGCGTCTTTAAACCTCTCTGTGAAGCAGATT
TGTACGTTGGGGCTTCAGGTACGACGATAATCAGCGCCATCGTGATCAAGCCTTTATCTAAATGGGTCACTTCCGGGCGTCTTTAAACCTCTCTGTGAAGCAGATT
GGATGAAGGGTGAACTAAGGCTCACTATTTGCGACCATTGAGTTACCACTCGGACAGGCACATTTCTTCGTCTACAGCGATGTCGATCAAGTTCAGGCTGGTGACTCCGA
TCTTGATGCCTCTTCCCGCCGTTCTCCATTTTCTTCTCCATACTTTTCTCTATTCATCTGCTGAAAATACACCAAGGTGGATCCGTTGCTAAATGTAACTTCCAACTAATCTCGTTT
GGCGCGCACCTCTTTACGACCGTTTCCCCTTCTGCAGATAGGCTGTCTTCTTCTCGAATTTGTTGATGGACTTCTCATCGTGAAGATCAACGATTACGTGATCTTTTTGCTGTAGTTCCCTGATTGA
GTTCTGAAGCGTCCTTCCTGCAGATGGTCCTTTCTCGAATTTGTTGATGGACTTCTCATCGTGAAGATCAACGATTACGTGATCTTTTTGCTGTAGTTCCCTGATTGA
CTCACTCTAGGGTCCAGAAGATGATTAACTGTTCACCCTATATCCATCTGGAAGATCTCGAGCAGATTTCTTAGTTACCATTACCACCAAATGTTATTCTTCG
TTACTCATTAGGGTCCAGAAGATGATTAACTGTTCACCCTATATCCATCTGGAAGATCTCGAGCAGATTTCTTAGTTACCATTACCACCAAATGTTATTCTTCG
GCGTACATACCGCGTGTTTCCCCTACCATTGGATTCTCATATTCCTTGGTTGCTGCCGACGCAACATTGGCGTTGACGGGAAACATTGGCCTTGAAGCTAGGGCCTTATCTTCTTGCCTTCAGGCTGTTCGGCAGCCTTAGTTACGATTACCACCAAATGTTATTCTTCG
ATCTTTATGACAAGATCATTGATGCAGATGGATTCACTGAAGCGAACATGGCTTAGATACGTTCTCACATGTCGTACTGCTCATCTGACCGTCATCGGGATAATCAGCTCAGTCTGCCTCTACCTATTGGACTCAGCTCTC
TTCCCGTCACCCTGTGATGTGTATCTGACGACCTTTGCGTTCGTCGACCTTTGATACTGCAACATGGCGTTGGGCGACGGAACATAACGCTTCATGAGGGAGGTTGCCAGAATGAAGCTTGGCGAATAGTTCACAATGTGGTGATGC
ACCGGAGCTGATGTGTATCTGACGACCTTTGCGTTCGTCGACCTTTGATACTGCAACATGGCGTTGGGCGACGGAACATAACGCTTCATGAGGGAGGTTGCCAGATAGTTCACAATGTGGTGATGC
CAATGTTAAGACGCTCTTCTTACAGCTCAATTTTATCCTTACTCCTGCTCTTTCTGAGATCGTTGTGAGATTAAGACGATGGATCCATCTTTCG
CGTTGGGCCGCATTACGCTGAACCTTTATTCAAATTTAATGCAGTCGGCGTAGCCTGTAGCCTCTCATCGTTTCTCTGTGTTGATCATCGAGTCTGTCTGTTCTGTTTCACTTGAACGTCA
TGGCTCAATTACGCTGAACGATGCGCGCTAGCCTGTAGCCTCATCGGGCGCGTTCATCGGGCGCGTTTCATCCGCAGCTCTTCATCGTTTATGAGGTTACCATTCGTCACGATTG
TTCAGCTGATTTGACTCACTGCTGGATCTCTGTGCGTCCCGGCTGCTTTATCGGGCGCGCTGTAGGCTTTCATCCGCAGCTCTTCATCGTTTATGAGGTTACCATTCGTCACGATTG
CTACAATCACTGCTGGATCTCTGTGCGCTCCGGTCGATCTCTCATCGGGCGCGCTGTAGGCTTTCATCCGCAGCTCTTCATCGTTTACACATCACTTTGATTTCCGGCCAAACTGGACACATCTCTATCGGG
ATTATTCAGGTCGGAATTGCTTCATGATTGTATCGATTAAGCCTCAGAGTCGCTCAGAGTCTTATATGCCTCAAGATCTGAAGCCAACTTCACTGCTCCTGTTTGTGCTCTATATGCTCTATCCGCGGCATACCAACTGGACATCTCTATCGGG
CACAGATCGGAATTGCTTCATGATTGTATCGATTAAGCCTCAGAGTCGCTCAGAGTCTTATATGCCTCAAGATCTGAAGCCAACTTCACTGCTCCTGTTTGTGCTCTATATCGCTGATACCAAGTACGAAATTTACA
GAAAAGATCAAACTCCAGGTACCGAGTAAGTTCACCCGTGACGCCCCACGTCTTGGTTGACAGTTGACAGTTGACAGTGTAGTACATGCGTTGTCGATGGTCGCGCCTTCATTCTTCATCGAGGAGTGGCCGATTC
ATTTATCCGAGCTACGATGGTGCGACTGGACTGGAAGTCACGCCCCGCCACGTCTTGGTTGACAGTTGACAGTGTAGTACATGCGTTGTCGATGGTCGCGCCTTCATTCTTCATCGAGGAGTGGCCGATGGTCC
TGTGAACTACGATGGTGCGACTGGACTGGAAGTCACGCCCCGCCACGTCTTGGTTGACAGTTGACAGTGTAGTACATGCGTTGTCGATGGTCGCGCCTTCATTCTTCATCGAGGAGTGGCCGATGGTCC
ATGGCCTGGTGAGAGCTAGACGACCGGGCCTCCAGTAGAAGGGTGTTACTCATC
```

FIGURE 7

SEQ ID NO: 6

GCTTTTCTCGACATGGCCTATCTAGCCACACCTGTGCTAGGAGTCGGTTCTCGCATTACCGCCTTAGATCGTACTATTGATGCTATCACGTTGAAACCTCGAA
TCGACCTCCAAGATGTGATACGCTTGATCCCACACTGACGCTTGCGTCAGATAGAGTTAATCTCTTCGGAACTTCAAAGACGATATCGCTCGTGGACTATT
GCACCGGGACTGGCGTCGTCAATCCACCATTGTCTTGTGCTCCTTCCCGTCGCTCTCCGTCGAGTATTACTGCTAAACCCTTCGTCTAAACCGCTACCTGTTA
GATCGCTCGACTCAAAGATTCAAAAGCGACCAAATGATTTCGTGTTCAGGATTTCTTTCGCCATTGATTACGGACACTACGTCAATCGCTACCTACT
CTCGATGGCTTAATGCTCATCCGTGTACTCTACCGTAAATCGCATACTGATCGCTCGTTGTGCCCACAGCTCGTGTGTATGTTGTTTCCCAGCGCTTCTACTAGT
TGATGTTCTTCGTGAGTTATCCATTTTGAAATCCACTGTTCAAAGCAATCAGTTAGCATACAGTCAGTTGTCAAGCATCATCAATATCGTGTCACCGCT
AATTGTGTACTCACTGACGTTGAGCGTTGACCGTTCAGCTCTCTTGGAACTCGGTCGTCAAGACGTTGAAAGTACAGCCGATAGAAGCTCGAGTGCAGTTG
CGCTATCTCTCTGATCCTCTTGTCTCAGCTCTCCGTGCATTAACACCTCCCGTGATGACACCTCGTTGTGCTTGCTTCAAGTCGTTGATCTTAGGCTACAGTGTCGTCATTCCCCACTGA
GCATCCGCGTACAAGCGATGACAACCTCCCGTGGCATTAACACATTAATTCAAGTCGTTGATCTTAGGCTACAGTGTCGTCATTCCCCACTGA
AAGGCCATTCCCGTTGTCGGCCTCTTGTGCTTGTGCTCCTCTACTCTCCACTGTTGCTTCAACATTTGGATTTAACATTATCTGATGACTGGGTGCCCATTCCCAGCTCATTCGTGATCATACAGGT
ATGTTTGAGATGTGGTTACAGCTCAGTCAGTCACGTGACCGTCCCAAATCGTTGGCAGCTAAACGCATCTGGACGGATAGAATTCATTGGACGTGTATGCCCAA
CAATTAACTATGTACAGTCGACCATGATTAAATTCTCACTGGACTAGAAATTTGCGCACGCGAGTAATGTACCCGGAGTCGATGGACAGTGATGACGTGGGT
GACGCTTTGGATCCTACTTTTGCATCCCACAGTACCCGACGTCTTGAGCGTTCTTGACCTTGTCAATGAGTTGCTGACTCCCAAAGCTTCAGAGTTATACTCGGAGCGTAGTGTCG
AATCAGGAGTATGTTGCATCCCACAGTACCCGACGTCTTGAGCGTTCTTGACCTTGTCAATGAGTTGCTGACTCCCAAAGCTTCAGAGTTATACTCGGAGCGTAGTGTCG
AATTCCGATCTCTCACTTACGGCGCGTTGGTGGTGACTATTCCAGGTTGCGCTGAGTCGCTGTTATAAGATGTTCGCTACTTCTCGTGTGCTCCCCTGTCA
TATCCTCTGCTCAAGTCGTTGTTGTCCCCTGATTGAATCTGCCCCACTGTTAGCTACGTCACCCTTCTCGTGTGCTAGCATGCATGTATATCCCTT
TTGTTCCTCAAGTCGTTGTTGTCCCCTGATTGAATCTGCCCCACTGTTAGCTACGTCACCCTTCTCGTGTGCTAGCATGCATGTATATCCCTT
CCTCGTACTGGAGCGGACAATGGCTGGTGACTGTGACACTCAGCGTCACGCACATCTCTAGTGGAGTTGGGCGCTAAATCCGTGCAGTTAAAGTATCCGTTCATTGGACATCT
ATTTGATTGGTCTCGCTTTCGTGCGACTATAAACGTAGAACACATCGTGCGCTTTCACTCCCTTCCAGCACTACCATTGAGTCTCCATTGAGTCTCCATTGGAGTTAAAGTATCCGTTCATTGGACATCT
CAGAAGCCACTGTGGACGTTTTGACAATCGTGCGCTTTTGACAATCGTGCGCTTTCACTCCCTTCCAGCACTACCATTGAGTCTCCATTGAGTCTCCATTGGAGTTAAAGTATCCGTTCATTGGACATCT
TTTGCAAGAACATGAAACTATATTGTCGACGGTTGGAGGCGAGCACTGACGGGCGTGACACCCAGGAGGGTATGCTGGTAACCCTGGGTTA
GTCGTCTTGAGATACTCATC

FIGURE 8

SEQ ID NO: 7

GCTTTTCAGTGCCTATCTTTCTCACAACATGGGTAACGCGACGTCTGTAGTACAGAACTTTAACATCCAAGGTGATGCAATCACTTTGCACCTTCAGC
CGAAACCACATCACCGCTGTACCCTCCCTTTCATTAAATCCGGTTTGCTCAATCCCGGCGGCAAAGCTTGGACTTTGATTGACGCGTCTCTCAATGCA
TCGGATCCATCTTCCCTGCGGTTAATGACTTCGGCTGATCTGTCTACGCTGTCCCAATCTGCTGTTGGTAATTCTACTGGATTCCTACCAACTTCGGCA
TGTATGCTCTGACCACTAAGGAGACATTAAGTGTTGTGACGGATCATGCTATAGCACAGTTGAAAAATTGCAGATGGCCTGAGTTAGATCGTGATTA
TTTGGATGCTCGGCGTATCACCTGAATCTGTTAACATCCATAATAGTGTATGTCGACTGTTTCGTGGGCGTTTCTGCTCGCCAAGCGCCATCA
AACTTCCAACAACGTGTGCCAGTTATATACACCAGATGACTCAAATCCAGGATGATGACTCTACAGTAGTTCGTCGTCCCTGGGAGCGTG
ATATTCGTGAATTGCTTACTATCATAACCCACTTCTACTACCCTGGCAAGTTATCATGTGACATGAGGTCAGTAGTTAGTTTCGTGATAGTCAGCTATC
AGATACGAGTTTGTGCCGCCTCTACCCAGAATGTGCTGCAGCAGCCCTTGCTAATACGTTGGAAGCAGGCTGATAGTGATGAAGCC
CCTTCTCTGCTACTAATGACATAGCTGCTTCAACGATGGGAGCTCCCGAGGCCTCAGGCTAATATGAGCTCCCGTACTGTGAACCTAAATCTTACAATATTAG
GTCTAGTGAATGATGTGGGCGTAGACATTAATGGCTGCGTTATGCTGTGTGAGATCCTGTCATCATCCGAAGTCTCTCATACACCTGATCAAACTACCCAGAAGCAT
GACACTTCGTGTGGAAGAAGGCTCTACTAAGTGTTCTCTTCTGATCAATCTTGAGCAAAACGTGTCGAAGTAAACGTGTCGAAGATTACAAGAAAGCTCTT
TCGATCCTGATAATCATAAGTGGTTTCTTCTGTATGATGCCAATCCAAGATACCCTTCAAGATCTTGGACAGGGCGTCCACTATCCTACTGTTTGAGAGAAACGGTTACC
AGCCGAGGTGACAGTGCACGCAGCTGATAGTTCCTATGCACGTGACAGTTCCATGTGACGACCCTGAAGATCATAGGGGAGACGTCACTATCCGTAAGATCATAGGCGACATGGATGCAA
ACCGCCAACACTGAGGTTAACACTTACCTCGGGAACTGCATTAACTCGGGAACGATGCCGGCCTTATACTCGCGGATAAAGCTACGAAGCTGGCAACCGTTGGTACACCGTTATCTGTTATT
AGCCCTTTCCGCAGCCCTTTAGTACTCCGATTCAAGTGTGTTAGCGGTGTTCAGCTTTGCATATGTTTCGGTGATCCCTACTAAATCATTGTCCGCGGAGTGAGATCTGTTATAATACCGGCAACAGTCC
GATGAATCGTCAAAACGTGTTGCCTCTCGAGCTTTGCATATGTTTCGGTGATCCCTACTAAATCATTGTCCGCGGAGTGAGATCTGTTATAATAACGTCACCGCCAACACAGTCC
CGTTTCTAAAACGTGTGCCTCTCGAGCTTTGCATATGTTTCGGTGATCCCTACTAAATCATTGTCCGCGGAGTGAGATCTGTTATAATAACGTCACCGCCAACACAGTCC
CTGGACTGGATTCATTCAAGGCGTTCTGACTAAATACAGACGTTGTTCAAACCATCGTGAGGTGCTAAGGCCCTCTCCCGCGGTCGGTGGGCACGT
GTTCAAACGTGAAGCAGGGTTTCTGACTAAATACAGACGTTGTTCAAACCATCGTGAGGTGCTAAGGCCCTCTCCCGCGGTCGGTGGGCACGT
CGTGGTGATGCTGAAATGCACGGGGGTGACGCCCTCTGATTGGCACGTTACTCATC

FIGURE 9

SEQ ID NO: 8

```
GCTTTTGAGTCCTAGCCGTGATCATGGCGTCAACCAAGTGGGAGACAAGCCGATGTCGCTCTCAATGTCTCACGATGATCATCTATCCGCAGTGCTG
CCTCACAGTTTTGTCGGTCCCTCGTCTCACTCAACGCCTATCCCACCTCACCCGTCTGTTGAAGACCGTGCTGTTGAAATTTATGATTGGCGATCTGGTTAC
CGTTCAGGGTGCCCTCGCCCCCGTTTGATGAGTATTGGTACGATAACCAACCTCTGCTAGCTCAGGCTGTCAGGCTGTTGAGATGCTTGCTTCTGAAGATCGTTTACGT
CAATTCGAGCATTATGAGAAATTCTACTCAAGAAAGGTCATCAGAAGTCTGAGATTATGAACAGGTTACGCCCTCTTTTCACAGACGTTCTTAAAGTTA
AGATGGAAGCTGAGGCTTTACCTGCTTAGCTCAAGCAGCAGACTATTGCTAAATCTCCTGGCCGTCTCGATGAGGAGAATACAACGTTATCGATCGCGTTTCCTGACGCAC
TACCTCAAAGGTCGTGACTAAGCACAGCAGTCTAAAATCTCTGGCCGTCTCGATGAGGAGAATACAACGTTATCGATCGCGTTTCCTGACGCAC
GAGGTTTTTGATCTGACGTCGACTTACCCGACTGTGCAACCTTTCATGAGTGCAACTTTCATGGATATGTACCGTCCCTGCGCCGCCATTCAGGATGTGTGT
ACCGTCGCAAGGCTTACTCATTCACTCTCCGATGAGCAATTCTCAGACGTTTCTGACATCGCGCCATCTCATCAGTGCAAGAGGAACGTACTCTCGGACC
GGCTGGAGATGTCGTCGGCGTGCTAATAACGGCTAAACGATCATCTCACCCAGTGCGCTTCGTTGGGCGATTGACCAAGAGGCCGTATCCTCGGGGGCCTTAAAGCAGTCG
AGTAAATATTCGAAATATCCGTGTTTGTTGGTATCGATCCCCTGGTAATCTCTCTCGTAACTGCTTCTCGCGTAGAGATCTCCATCGTCATCCACCCATGTACCGGATCCAAAATTCTGACCTCCA
TTTCTACTCGAAATATCCGTGTTTGTTGGTATCGATCCCCTGGTAATCTCTCTCGTAACTGCTTCTCGCGTAGAGATCTCCATCGTCATCCACCCATGTACCGGATCCAAAATTCTGACCTCCA
ACTACCATCAGCAGCCGTGCACACTATCGATGTGAGCACTATCGATGTGAGCACTATCCAAATCTCGTCCTCGCCTAACAGATACGGATCTCCTACCGATCTCCATCGTCATCCACCCATGTACCGGATCCAAAATTCTGACCTCCA
GCGGTCAGTTACTGAGCACTATCGATGTGAGCACTATCGATGTGAGCACTATCCAAATCTCGTCCTCGCCTAACAGATACGGATCTCCTACCGATCTCCATCGTCATCCACCCATGTACCGGATCCAAAATTCTGACCTCCA
AACTGAAAGAACAAATTACCAAATCTCGTCCTCGCCTAACAGATACGGATCTCCTACCGATCTCCATCGTCATCCACCCATGTACCGGATCCAAAATTCTGACCTCCA
GCGTGCTAATAGGGAACTGTCACTGAAGGCCAGTGCAACTGGTCAGACATGGAAACCTCAATGATCTCCTCTATCCTTGACCAGCGTATGAAGAATCGTGTGCGTAAATGCT
AGAGATCATGAGAAGGGTCTGCTTCTCGCCTGAATGGGAACCTGAATTACTCCAAGAGTTGGCCAAAGCTGACCACCTCGCTGTGGAACAGGACATGATGAC
CTCGGCTGCGCAGCCAGTGCTAAACGAGGCCATGAGAGGCCATGAGAGCCCGGATGAGCCCGGCAACCTCGTGTTGACGAAGCGCTTTCGTCAGCGACATCGAGCGCCGCCTAATGCGCTTG
TCAGTCTCTACAGTACTTAAACGAGGCCATGAGAGCCCGGATGAGCCCGGCAACCTCGTGTTGACGAAGCGCTTTCGTCAGCGACATCGAGCGCCGCCTAATGCGCTTG
AACGCTGACAATCATCGGATGAGCCGGCAACCTCGTGTTGACGAAGCGCTTTCGTCAGCGACATCGAGCGCCGCCTAATGCGCTTG
CATCTATGGAAGAATTGGTAGATGATGTGAGTCTTGACTCGTCTCGATTCCATGACTCGATTCTCTCGATTGTGACTCGATTCTCTCGATTGTGACTCGGGACTCGGTTATTCATC
```

FIGURE 10

SEQ ID NO: 9

GCTTTTCAATCCCTTGTGTCGATGTTCCGTATGTCATCTGGTTCATGTAACGTTGCAACTTCTATTTTGGTAACGTTCACTGTCAGGCAGCGCAAAA
CTCGGCGGGTGGTGATCTTCAAGCGACTTCCTCCTCTCTTGTGCTTCCTCTGTGCCTACTTGGCGTCTGCGTGGGCGGTGTCTCGTTGTTATTATAATTGTT
GGCGCTGTTGTGTTGCAAGGCTAAGGTTACGACGCAGCCGAAACGTTTCTACCGAGAGCTGTTCGCACTTAATTCGGTAAAGTGATGCAG
GACCTCCGATTACCAGGTTAGTGTACGAGATTTGAGTTTCGTCGTCCCCTTCACCTTCGTCTCCAGCCTTGTCTCACACTGTTCATT
ATCCGGCTCTCTACTTTAACATTGAGTTTCCGTCAAGTCATCGTCTCAAGATACGACTGTGCGCATCCATCAACGCTATTACGACGATCCCTACACCA
GATTCGGAGATTCGCTCTCGTGATTGTTCATTGGAAGGCTTAACTCAGTCACAGGAAAGAGAGGTCGTGGGCTGAATGCGTCGTTGAATGAGATCATTAACTCTCATTGACTTCGAACGTG
GGTGCGTCATCATCCTGGCGATTTGACGAAGTTGGGCAATGCGCGGGGGTCGTGAGTTGGCAATGCGTCGTTAGAGATCATAAAAGGCGTGTAGATC
ACTATAAATCCTGGCGATTTGACGAAGTTGGGCAATGCGCGGGGTCGTGAGCCCTACGAGAGAGCTGAACTCGTCGTTGAACTGAATCGTCCGAACTACGACCTACTACTAAAGCCCTCTCGCCCACGAATCGAGGAGTATGGCGGGT
ATCTCTTTGGGATCACTCACGGACAGTATATCGGATCTTTCTAGCCAAGTGACGATCTAACGCCTCTCGCCCCACGAATCGAGGAGTATGGCGGGT
CTTATAGCTGATGTGACTAATCTTAAACGTGACGTATCCAGGGTCTTCAAATGACGAGTCTCGAGCAGCGTGTAACTAGTTTGGAATCGTGGTACTG
GATCTATTCCCACATTGCTGCTCCCCCTAAATTAGAATGGCGGGATTGTTCACTCGATCTGGACCCTTACTTTGTTCTGTGACCATAATCTCACGTC
GTATTCGGCAAGCGCTCTGCTAATGAATTTCAGTGGCTTGTTCGAGGGTGGCTTGTTCGAGGTGAGGGAGGTCGTCTGACTTAACGTAACGTTGATCTTAATGCGCTTATTCTCCAC
GGCCAGGAGACAGATTTATGATGTCGAACATGTCATGCGCATTTCGCTTGACACAACTCTCCGCAATTCTGTAATGTGACAGCTCATAGCCAC
CCTCCGACTATTCTCGCTTGATACCATGTCGAACATGTCATGCGCATTCGCTTGACACAACTCCTCCGCAATTCTCCCCCTGCAATCCAGTACCCTGCGGTCATACGTTCATAACCGTGCGTACGGGC
GGTATGTTCGACACAACTCCTCCGCAATTCTCCCCCTGCAATCCAGTACCCTGCGGTCATACGTTCATAACCGTGCGTACGGGC
ATCGATACTTAAGGTGGGCCGTACGGGATTGGTTATTCATC

FIGURE 11

SEQ ID NO: 10

GCTTTTTCTCCCACGATGGCGGCGTGCCGTATACGACTTCTTTTCTACGCCTTTCGGGAATCGTGGTCTAGCAACGAATCGTACTCAACTATCATCACTAC
TAACAAGCTCGAATTCCCCATGGCAACGATTCTATCTTCAATGACTCCATTGACGGCGCCAGGTATTGTCTCAACACCTGAAGCACCCTATCCGGCTC
ACTGATGTATCAAGAGTCCATGCTTCACAGTGCCACTGCCCTGGAGTACTGGTAATCGTGATGCTTGGCGTACGTTTAATGTCTTCGGGCTTTCATGG
ACTGACGAAGGACTGTCAGGACTGGTGGCTGCTCAAGATCAAATCAAAATACCCGCTTCTGCTATCAGCAGCTCTGCTTGCCAGTGGTCAGATCCTCAACTACC
CCAGATGGGCGCGAACAGACAGAATATGATCTCAGGACGCGGCTAGCAACTGGTTCATGTCCAATATGCAACAATTCGTTGACATGTGTGCCAGGTTGACACAGTCT
TGTTTGAACATGCCTGTCGAACCTGATGGGAATTACGATCAGCAGATGCGTCTTTGATCAGTTGTGGCTCCTTTCGTACATTCGGGTAGTCAATCAGA
CTAATACCATCAGCGGCTTCGCTTACGTGTGCACGTCCCCCTGATTGGAACGTGGATAAATCGTGGACCTTATTTTACACCACAAACACCAATCGTGTCCAAAT
TACCCAGAGAGCATTTCGCTTACGTGTGCACGGTCCCTGATTGGAACGTGGATAAATCGTGGATCGCTGCGGCGAATTTGACCGCTATCATCATGGCC
TGTCGTCAACCGCCAATGTTTGCCAACCAAGGCATTAGGACACAAATCAAGGCAGTGGTCGTGTCAGCGGCCAAGGGCAAACATTAACACAAGAGGCTAATGACTT
ACTTACTGACTACCCGCGAGAATGCATTAGGACAAATCAAGGCGCAGGATGATGCTCTGTACAATCAGCAGCCAGGATACGCAAGGAGATAAAACCCTTCGTT
TTCGCCCCTCATCCAGCAGACACCCGCAAGCTCGGCCGTTCTAGCCACTTTACCGCCGTAGCAGATCACGCGTACGCTGCCCCAGTCCAGCCCTC
AACGGTGACTGGACACCAGCATGACCCGCCAAGCTCGGCCGTTCTAGCCACTTTTACCGCCCTAGGCGTAGGTCGTACGCTGCCCAGTCCAGCCCTC
CGGCAGCCACGTGGGTGTACTCATC

FIGURE 12

SEQ ID NO: 11

GCTTTTTGAGTCCTTAGCGTGCAAGCCGCAATGGAGTACGTGTGCCAAACTTTCACTCGTTCGTTGAAGAATAACATCCAGTTACTTACAGACTCCTG
CTGTTGGAATGCACAAACAGCCTGGGACACTGTGACCTTTCATGTCCCTGATGTCATTAGAGTCGGTAACGCTACTGTGTCTCAGTGCTGCGGTGT
ACTTTACGGAACTCTGCCATCCGACGGGAATTACTTCCCTCACAAATGTCATCAGCAACAGTTTAGGACTGATACCCGCTACTGCGATACGTA
AGGATCGGCAGAATGATGAAGTTACGCCCATGAGACTGCTGGATCAGTCGTATGCCGTCTATCGCCGAACACTATGATGAGACCCGGCCAACGTATGGTTGATG
AGCCTGAGAATGATGAAGTTACGCCCCCTTGACATCGTAACGCGCAGCTCGCGGATATCGCCTCAGCATGCTGGAAAATGATTGATGCGTCCTCACGTAGTCTGACCCTCCCAACTGTCTTGTT
TGAGCGACGCTCTGATGACTCTGTGCATTCACGTTCCGTCTTTGGTCAAATGCAAACGACCACCATATACGATGTGCTCTGGAAAGGCAGTTAAGTTTCTCCGA
TCTCCATCTGTGTCGCTGTACCCCTCGCTCAAACGCGATGCTGGGCGATTACAGGGCAATATGCTCGGAGTCATACCACCGTGGTCATCCGCTTTGCCGCGTATACCGTTTTGGACATCACACTTTGCCTT
TGGTTGCTACCCCTCGCTCAAACGCGATGCTGGGCGATTACAGGGCAATATGCTCGAGTCATACCACCGTGGTCATCCGCTTTGCGTGTCATCAGGTATGGAGCCTGAATTGGAGCCTGAATGTGAGTCCGTTTGA
TTCGCCACTCATTGGTGAGTCATGGAAGCGTCTCGACGGTCTCTACCAAGTGCCTGAAGTCCGCTTTGCGTGTCATCAGGTATGGAGCCTGTGTGCTAGCATCTCTGCAGAAGAC
CACTACAGAAATCTGTTCATGGAAGCGTCTCGACGGTCTCTACCAAGTGCCTGAAGTCCGCTTTGCGTGTCATCAGGTATGGAGCCTGTGTGCTAGCATCTCTGCAGAAGAC
GAGGACACGCCCGCACCATGCTCGACGGTTGGTTGGTTGGTAAGTGCCTCCCGGGTCAAAATGCACATAGCCACCTATGTGACGGTTAGCGGGACTCGCCTATTCA
TACCAAATTCACTGTGTGGAGTGGTTGGTTGGTAAGTGCCTCCCGGGTCAAAATGCACATAGCCACCTATGTGACGGTTAGCGGGACTCGCCTATTCA
TC

FIGURE 13

SEQ ID NO: 12

GCTTTTGAGTCCTTGTGCAGCCATGGACAACACCGTGCGTGTTGGAGTTTCCCGCAACACATCCGGCGCAGCTGGTCAGACTGTTTTAGAAACTACTA
CCTACTACGATGCAACATCTCAGCTGACGGTCGTAATGCAACAAAGCTGTGCAACTCCCACTTCCATTCCTGTCGATGCTTATCTCCT
CTAGCTGCTCATTGTGCCGATAGGACTCTCCGTCGTGACAACGTGAAGCAGATTCTCACTCGTGAACTACCATTCCATCGGATCTAATCAATTACGGC
ACCACGTGAATTCATCCTCGCTTACTACTTCTCAGGGTGTTGAGGCAGCCGTCTCAAGTTATGGAGAGCAACTGTCATTTGACCACATCTA
CCCACTGGTTCTGCAACATACTGCCCTGGAGCGATTGCGAATGCGATCTGTCGCGTATCATGGCTGCTTCGTCCCCCACGAAGGCGTCCGCAGATTGTTCTCC
GATGGTGCCATCGATTATCTCGCTGACAACTGTTGAGGAAATGCGAGATCCAATTGTGTCCTCTACATGTCTAGACATGTGACGGCGTCCGCAGATTGTTCTCC
CATCTCACACTGTTGAGGAAATGAGTTCTCGTTCACTTAATGACTTGAGGATCACGAGCAGAGGGTCGAATGCCTTGACATCTTTGGTCTCTGTTCAACCAGATGT
TGACGCGGCTGAAATGAGTTCTCGTTCACTTAATGACTTGAGGATCACGAGCAGAGGGTCGAATGCCTTGACATCTTTGGTCTCTGTTCAACCAGATGT
CAACTGAAGGTGGAGCTGGAGTCGATGAGTGAGCTGGCTCTCTACTCATTAAAGAACAAGGTTCGCAATGAATCCAGGCAAGTGCATCTAAATGGTC
CTGCTTTGTCCCGATTGATCGATCGGTCCCACTCGCCCACTCGCCACGCGCCAGGCGCGCCTCAGGCGCGCTCAGGCGCGCTCGCCAGGCGCGCCATTCGTGAAGGTGACCAGACACTTCTG
GCTGATACGACGATCTGGTCCCACTCGGCGTAAACGGGACCCATGGCGTAAACGGGACCCATGGCGTGCGGGTGAGGGCCGCCACACCCCTGCCGCGACCCTGCCGCCTGCCGCCGCCACACCCCTGCCGCGACCTGACCTGACCCTGCCGCCTGACCCTGCCGCCTGACCCTGCCGCCTGACCCTGCCGCCTGACCTCTTATTCATC
TCTGTCTCTCAGCTAGGATGGCGTAAACGGGACCCATGGCGTGCGGGTGAGGGCCGCCACACCCCTGCCGCCTGACCTGACCTCTTATTCATC

SEQUENCE LISTING

```
<160> NUMBER OF SEQ ID NOS: 12

<210> SEQ ID NO 1
<211> LENGTH: 577
<212> TYPE: DNA
<213> ORGANISM: Artificial Sequence
<220> FEATURE:
<223> OTHER INFORMATION: Reoviridae

<400> SEQUENCE: 1
gtggtctagc aacgaatcgt actcaactat catcactact aacaagctcg aattccccat      60
ggcaacgatt tctatcttca atgactccat tgacggcgcc aggtattgtc tcaacacctg     120
aagcaccctg tccgggctca ctgatgtatc aagagtccat gcttcacagt gccactgtcc     180
ctggagtact tggtaatcgt gatgcttggc gtacgtttaa tgtcttcggg ctttcatgga     240
ctgacgaagg actgtcagga ctggtggctg ctcaagatcc tcctcccgcc gccccgtatc     300
agccagcctc tgctcagtgg tcagatctcc tcaactaccc cagatgggcg aacagacgtc     360
gtgagttaca atcaaaatac ccgcttctgc ttcgatccac gctgctttct gccatgcgag     420
ctggtcctgt tctttatgtt gagacgtggc cgaatatgat ctcaggacgg ctagccgact     480
ggttcatgtc ccaatatggc aacaatttcg ttgacatgtg tgcccaggtt gacaccgttt     540
tttttgaaca tgcctgtcga acctgatggg aattacg                              577

<210> SEQ ID NO 2
<211> LENGTH: 576
<212> TYPE: DNA
<213> ORGANISM: Artificial Sequence
<220> FEATURE:
<223> OTHER INFORMATION: Reoviridae

<400> SEQUENCE: 2
gtggtctagc aacggatcgt actcaactat catcactact aacaagctcg aattccccat      60
ggcaacgatt tctatcttca atgactccat tgacggcgcc aggtattgtc tcaacacctg     120
```

```
aagcaccota tccgggctca ctgatgtatc aagagtccat gcttcacagt gccactgtcc      180
ctggagtact tggtaatcgt gatgcttggc gtacgtttaa tgtcttcggg ctttcatgga      240
ctgacgaagg actgtcagga ctggtggctg ctcaagatcc tcctcccgcc gccccgtatc      300
agccagcctc tgctcagtgg tcagatctcc tcaactaccc cagatgggcg aacagacgtc      360
gtgagttaca atcaaaatac ccgcttctgc ttcgatccac gctgctttct gccatgcgag      420
ctggtcctgt tctttatgtt gagacgtggc cgaatatgat ctcaggacgg ctagccgact      480
ggttcatgtc ccaatatggc aacaatttcg ttgacatgtg tgccaggttg acacagtctt      540
gtttgaacat gcctttcgaa cctgatggga attacg                                576

<210> SEQ ID NO 3
<211> LENGTH: 3958
<212> TYPE: DNA
<213> ORGANISM: Artificial Sequence
<220> FEATURE:
<223> OTHER INFORMATION: Reoviridae

<400> SEQUENCE: 3
gcttttctcc gaacgccgaa atgagttcgc gcaaagtggc tagacgtcgt cataaggatg       60
ctactgaatc taaagacact aagaacacta ctaagtctaa gccatcttcc actgacgtta      120
aagaatccgt agaaaacgcc acagacaaga agtcaccgt cccaacgcca gataatccag       180
ctgcctctac tccctcctct actgatgggg cttcacaaac ctcagtcgct aagcagacga      240
atgataatga taactcggtt aaggaatcag ctcccaaacc tactgtatct agtgatggga      300 agatggaat gcacggtgcg gtgaaatcgc aagacgctaa agcgaccgta gctgtagata       360
ataataagga tagagacgta gtatttggtg gtgcgggttc tggtgataag aatgctatta      420
cgaagactgg gtctgttgac aatgatgggg gtgttaaggt tgttccagct aaagacgcta      480
cgatatcttc agctaaagct atgatggagc aaaagcagct tgtagctggc cttccgaagc      540
aaccgaaatc cgctaatcat tgtgtactg tctgcatggc ccagttcgcg tcatctgacg       600
ctcttgctat tcaccagact acgcattcta ttggttctaa tgctgctctg acaagctttt      660
cgatttctac tgctgttgaa gaattcattc agtcatgggc taccgccacg tctacagcca      720
acactaagac ggctttgact gtgtctgacg ttgactcact gatgatgact gaaggaatac      780
gcctcataac ttgggattcc gggttatgta catctttcga acttgtcccg attgtccatt      840
caaatactgt tcaagatgtt atttcttatt catggtttac gtcaagctac aacatcacta      900 cccccttttcc acaggcgact gtcgtacgaa tcgttttacg taccaactgg gctgctaagt      960
tggattcacc atcatcatcg cgggaatgtg atcttcgtct tgcccccct acagagagta     1020 acgctaggtc attctcgatg ctactcaaca cgggtgcgac cccagaaggc acttttaacc     1080
caaacactct tcgtatgaat gtgctgcaga tgtgtcttca gtatgtgctg tctaacttac     1140
acttaaaccg tagtactcaa tttaccatgg atttgactgc cgcggctcct aatctttccg     1200
cgtctcaact ccgtattgtt ccagaggata aggagggtaa atggtttcct gtcatgtatc     1260
catcccgagt gaacatcccc ttgttcaaca agactgctga tttcgtcaat cagtgcattc     1320
gtgataggat tggccgatat gatcgtgctc aaactttcgc tggtgcacct tctgaatggg     1380
ctgacatgtg ggagacagcg gactcgctaa ctctttccgt tcgtgaaatg tggatgtcgc     1440
gtatttctca gatgaacatt actcctgctg acattgctga cgctatctcc agatgttctc     1500
agtccttgct cactgttgct gcgcctacgg ctccctctgt ggctcgcttg ttaccgtggc     1560
```

-continued

```
gggttagttc tgatgaaagg cagctcctcc aattgttaat gtacctaaat gttgggacca      1620
gtgccgacta cgtccagccg attctgtctg cgtttgctcg gaccctgtct cgtgtgtcac      1680
cattacgcat taatcccacc ctaatcgcta acgctatgtc gacgatcgtc gagagcacta      1740
ctaacaccca gagtcccgct gcggctatct tgtcaaagct taaacctgtg gcctctgatt      1800
tttccgactt cagattggcg tgtgccgctt ggttatataa cggttgcgtt cagacatacc      1860
tgtctgagga ttcatatcca agtagtggtg ggtctgtcac tagcattgac acgttggttg      1920
atatgttcgt gtgtctactg gcgttacctt tagtcactga tcctaatgct ccgtgccaag      1980
cctttatggt tgtcgctaat gccatggttg gctacgagaa tctgcctatg gacgatccta      2040
atttcactca gcagagattg gctgcagcat ttaacaatcc taccacctgg cctcagtgct      2100
tccttcaccc tcaaaatatt gatcgtcgcc agtgtcccat cctctcctgg tgggctcagc      2160
aaatccaccg taattggcct acaccatctc agattactta cggtgcacct gatatcattg      2220
gatccgccaa tcttttcact cccctgatg tgctgctgct tccattacaa cacaggccca      2280
tacgtattac caatcccact ctgaacttcg ataatgagtt gacgacctgg cgtaacaccg      2340
tggtcgactt agtcttgcgc atcatcgaca gtggtcggta ccagcctaat tggaatcagt      2400
ccattcgcgc gtccatgcga aatgcgatga cgaatttcag gattatcaag tcttacactc      2460
ctgcctacat agcggaactg ctacccgtcg aattggcggc catcgcccca actttaccct      2520
tccagccttt ccaggtaccg tttgctcgtt tggatcgtga cgctatcgtc acccacgtca      2580
atgtatctcg gcaagctccc aacaatcttg ctcaacctgc gttaaatatg tctatgacgt      2640
accagcgcac aggagttccg atctctctca gcgcccgtcc cttagcggtc gctcttctgt      2700
caggccagta ccccactgat cctcctcttc agaccaacgt ttggtacgtg aacactctca      2760
cacctctgta ttctaatgat ggtctcttta acaacgtgca acatgcgatg gttgcctctg      2820
aagcttacgc cactttgatc actatgctgg ctcagtgcac tgacatgcaa tatcccgtgg      2880
atcgccctct gaactggttg cgtcagatta atttggctgc taatgaggcg acgattttg      2940 gtcgctcgat caattcactt ttccagactg cctttgacct ctcgccttct actgtgttgc      3000 ttcaacccttt cttggagtct gatccacgtg caacgcaact agccatttct tacgttcgct      3060
ataatggaga cagtgagacc ttcgtaccga cagtacggcc atctatgatc tcagaggcga      3120
cattgctcgt tgagcgcact cttttcgcatg aatacaatct cttcggtcta tgccgtggtg      3180
acatcattct gggacaacac atgactccga ctgcgttcaa tcccttagct cctcctcctt      3240
ctgtcatttt taacagggt gatgttgatg ttcatgaatt tggatctcgt agcttcgcta      3300
acttcggtat gaatggagag gagatcttgg tcatggacgc gaacggtgtg cgtcgtccac      3360
tacttggccg gtgggttatg ccgctccagc ttttgatggt gaatattggc gtatttccca      3420
agctgctgtt ggatcgtatc ttgaaaggac gtctatatat cagacttgaa gttggcgcgt      3480
atccctacac ggtgcagtac taccaggac gtgagttcac tgacggtttt acattgcttg      3540
agcaatggat gtccaaggtg tcgcccatgg gtatccctcc tgttccttttt ctcatgccac      3600 agtccgaggg acacaacatc acttcaggca tggtcactca ctacatctgg tccactgagt      3660
acaatgatgg gtcactcttt gccacgaaca ctgacctgcc ggttactgta tttgggcctg      3720
accgtaccat tccaatcgag cgctatcgtg cactcgttga tccaggcgcc ctccctgcta      3780
ctaaccaact gccgcacact atcgatctct actgctcact gagacgttac tatctggaga      3840
cgcctcccat tactgccact gtcactactt atggcgatgg actccccgcg ctgaaccatt      3900
agagcggcga ggctagacgc gagctgatcg cgtcgactct cgttggagat tattcatc      3958
```

<210> SEQ ID NO 4
<211> LENGTH: 3829
<212> TYPE: DNA
<213> ORGANISM: Artificial Sequence
<220> FEATURE:
<223> OTHER INFORMATION: Reoviridae

<400> SEQUENCE: 4

| | | | | | |
|---|---|---|---|---|---|
| gcttttcctc | accatgcgtg | tcaacgggtt | tgatgatgct | actctctctt | acgcacaatc | 60 |
| catttcgggg | gttattccta | tgacaaataa | gttatttgag | caagcatccg | catcaatacg | 120 |
| tgctttaccc | cgatcacacg | tttacgctct | gttagacgac | gttaatttct | ctgtttcatg | 180 |
| cgtaattcca | aatcgcatct | tccaccactc | tgaccactct | gagtattttt | acgttgatgc | 240 |
| ggttaataga | gttaggcgta | aacaggttat | tgatcctgat | gatgtgttcg | ttcctaattg | 300 |
| taatttacag | ggtctcatct | ctccaatgga | gaggttaccg | aattatggcc | agttatcgga | 360 |
| aattatttcg | tcgaatgcac | gtgacggcct | gccgtccgct | cgcatagcgg | ctacatttta | 420 |
| taatatttct | gtgtcccaag | ctcgtcagat | taaggctccg | cttgaaacat | ttttgttgcc | 480 |
| cttactgctg | tctgagacct | actctttatc | agaggatcct | tgtggtcttg | acactacagc | 540 |
| ttctcccccg | attcatacaa | atttagcgtt | atgggtgtta | cgtgaaatta | gtcgaactat | 600 |
| ttgtggatct | tcaaaggatc | gctcaccctg | gttgttactt | gactccggtg | ttgcgtggtt | 660 |
| catgtctccg | ttaatgtcat | cagctatccc | acctcttatg | gctgatttga | ctaatctagc | 720 |
| gatttacaaa | cagatctgtt | ccgttttctga | cgagatgcat | tctcttgcgg | ttcaaatggt | 780 |
| tttacaagct | gctgcgtcac | agtcatatgg | tcattacata | ttgcagacaa | agtcaatatt | 840 |
| tcctcagaac | accttacaca | acatgttttcg | gacgctcact | gatggcatcg | taccagtcat | 900 |
| tgattggttg | gaaccgcgtt | ccaattaccg | tttcatgctt | cagggtgcgc | gtagggtgac | 960 |
| ttcagatgat | gcgaatcaag | cgccggacaa | tacggaagca | gctgagcaac | tcggtcgtaa | 1020 |
| gatgggatgc | ttagatgttg | tgcgatctct | gcgtaagatg | tcttcatcta | ttactgttca | 1080 |
| ctcacatgat | gcgatgactt | tcgtgcgtga | cgccatgtcg | tgtactagtg | gtatatttat | 1140 |
| tacacgtcaa | cctactgaga | ctgttttaaa | agagtatacc | caagctccca | ctattgaagt | 1200 |
| gcccattcca | caatcggact | ggtcaccgcc | tattggatct | ttacggtacc | tttcagatgc | 1260 |
| ctgctctctt | cctgctgtgt | acttggctag | agcttggcga | cgggccgctt | ctgcagtggt | 1320 |
| agacaaccct | cacacttggg | atcctttata | tcaggctatt | cttcgctccc | aatacgtgac | 1380 |
| atcccgtggt | gggtctggtg | cagcgctgag | agatgcttta | aaggctgctg | aggttgagct | 1440 |
| tcctcaatat | cctggggtca | gtgttaaggt | agccactaag | atttaccaag | cggctcaaac | 1500 |
| tgcagatgtc | ccctttgata | aattatctcg | agccgttcta | gctccactgt | caatgggtct | 1560 |
| gcgtaaccaa | gttcagcgac | gtccaaggac | cattatgcct | atgaatgtcg | tccaacaaca | 1620 |
| gatttcggcg | gccacactc | tctccgctga | ctacattaac | tatcacatga | acctatcgac | 1680 |
| aacatcaggc | agcgcggtca | tcgagaaggt | agtcccactg | gcatgtatg | catcatgtcc | 1740 |
| tcctgctcag | gcggttaata | tcgacattaa | ggcatgtgac | gcttctatta | cgtatcagta | 1800 |
| ttttctttcg | gttattgtcg | gcgctattca | cgagggtgca | gcagggcgtc | gtgtctcgtc | 1860 |
| ctcatttatg | ggagtcccctc | ctagtgtctt | gtctgtcgtt | gattctagtg | gagtgacgtc | 1920 |
| gtcagtgcct | atttctggtt | ttcaggttat | gtgtcaatgg | ttggctaagc | tctaccagcg | 1980 |
| aggttttgag | tatcaagtca | cggacacatt | ttcgccaggt | aatatcttta | cacatcacac | 2040 |

| | | | | |
|---|---|---|---|---|
| tactactttt | ccctctggtt | cgacggcgac | gtctacggaa | catactgcta ataatagcac | 2100 |
| gatgatggac | ggattccttc | gcgcttggat | tcctgcttct | ggcgcgtctg atgtcttgaa | 2160 |
| gaagttctgc | aaatccattt | cgatacaacg | gaactatgtt | tgccagggcg acgatggtct | 2220 |
| aatggtggtt | gatgggttgt | caactggcaa | attgtcaggt | gaaataatcg atgaattcgt | 2280 |
| taaagagcta | cgggcttatg | gtaaatcgtt | tgggtggaac | tatgacatag agttcactgg | 2340 |
| gaatgctgaa | tatttgaagc | tatatttcct | aaacggttgt | cgtataccta acgtttctcg | 2400 |
| acatccaatc | tgtggtaagg | aacgagcctc | aggagacaaa | ctggagatgt ggccgtctac | 2460 |
| cattgacata | ttcaatggca | tatttgtgaa | cggcgtgcat | gatggcttac catggcgtag | 2520 |
| atggctgcgt | tattgttggg | ctcttgctct | catgtattcc | ggaaaaatcg tacgtcatga | 2580 |
| cgactctgag | gtgttaatcc | aatatccgat | gtggtccttc | gtctattggg gcttacctcc | 2640 |
| tatcagtgcc | ttcggttctg | atccttggat | cttctctcca | tacatgccta ctggtgacca | 2700 |
| tggcttttat | tcaatgttaa | cattagtgcg | tcccttgatc | gccgcctcgt ctccccgtc | 2760 |
| ggacgcttct | gggctattcg | gtcagtgcga | tcataacacc | ctgttcaact ctgaattagt | 2820 |
| atatcagggt | tactatatgg | cgcaatgtcc | acgacaacct | tctcgctcaa atcgtagaga | 2880 |
| tgatcccgat | tcggtgcaac | gttttgtcaa | ggctctagag | tcttacctgt acatctcccc | 2940 |
| tgaactgaaa | tcacgagtga | gacttggccg | tgatcgatgg | cagaaattgg ttggctacac | 3000 |
| ggagaaatct | ccaccttcgc | ttgatgacgt | agctctcaag | tggtttcgta gtgctcaaga | 3060 |
| ggccgatctt | ccgactgctg | tagaaattca | ggccatggat | ctgtccttgt tatctgcaag | 3120 |
| acgtcggaca | tatcagggat | tttctaaatt | attgaatact | tacttgagag tgacttggga | 3180 |
| cttgtccgaa | ccaattgacc | acgctgtgga | tccccgtgtc | cctctgtgtg ctggtatatc | 3240 |
| tccgtcgaat | agcgagccgt | tcttaaaatt | gtactctgtt | ggcccgatga tgcaatcgac | 3300 |
| acgtaaatat | ttcagtaata | ctttattcat | tcaccgtact | gtatccggtc tcgatgtcga | 3360 |
| tgttgtcgat | cgtgctcttt | tgaggttgcg | tgcactcaat | gcgcctgatg acgtggttgt | 3420 |
| agcccagctt | ctcatggtag | gtttatccga | agccgaagcg | gccacgctgg cagcgaagat | 3480 |
| acggacgatg | gatatcaacg | ccgtgcagtt | agcgagagtt | gtcaatctgt ctatccctga | 3540 |
| ctcgtggatg | actatggact | tcgaccgtct | gatacgagac | atagtgtcta tcactccgtt | 3600 |
| gactgtccgc | tctttaacta | ctgatctacc | gtccggtgtc | ccatgggcac gtgcgatact | 3660 |
| ccagttctta | ggtgcgggtg | ttgctatgac | cgccgttggc | cccgtgcgtc gtccctatct | 3720 |
| gcattcggta | gctggaggca | tggcatcgtt | cattaagcag | ttccgccggt ggatgcgtgc | 3780 |
| tgaaacgagg | tagcgtccgt | gcccggcatg | gctcgaggaa | ttactcatc | 3829 |

<210> SEQ ID NO 5
<211> LENGTH: 3907
<212> TYPE: DNA
<213> ORGANISM: Artificial Sequence
<220> FEATURE:
<223> OTHER INFORMATION: Reoviridae

<400> SEQUENCE: 5

| | | | | |
|---|---|---|---|---|
| gcttttccac | ccatggctca | gattagaggc | cttcggttgt | caacgacgct ctcagctcct | 60 |
| ccttcacgaa | agactttgac | ttcacataca | tacgatgagc | taatatctgc gttgaagcta | 120 |
| actaccaaac | catggcgacc | acttaagtct | agggatcgga | attccatcac cgcggtgcaa | 180 |
| ctattattcc | ccctcaatgg | atatatcgaa | ccaatgttca | tactggagaa agacatgagc | 240 |
| tatgaggatt | ttgagtcttg | gttatcacct | ctactttcag | ctttggcgga tcaattgtta | 300 |

```
cggcgttacc ccattgcgtc tcaccatggg cgactggtta atccattgct ttccaatgcc    360
atcgtcgcgg cctttctatc aaatgttcct tacttgcatg cgctggatca tcttttata    420 atccgcggcg ttgttgaaga cattctggat gtcggacttt ccattcagaa tcatctgtgg    480
tatgatcgta gtgcccttgt gacgccagct ggtcagaagt tcatccaact atctggttat    540
catttctcct ctcaagatcc ttgtttgttt tcaaagcaac tgcgttgcta tgggctcgtc    600
tattattttc tagacatgtc ggactgcatt tcatattgtc agcgacatct ctccaattct    660
actcctctta ttcatttcga tcgcccatct aatggagtac attgcttggt cccttccgaa    720
tcaacaactc caattgctgg ctccctacct gtgtcagcac tcagttctat cttgcttgag    780
tcttgtattc aacaatctct tctgaatact cgaactccta ccgggagtcc ggttgtgagg    840
caagttgagg tgttactacc tatttcgtcc cctttcttcg agcgtcaaaa tactttggaa    900
tactccttat ttgcgctctc taacgcgctg gttaatggct accagctaat agacttacaa    960
ccgaatcacc cggattgcgc gactgtagcc gctattttag ccaggctgat tgattttcg    1020 aaggacatta ctaccattcg cccatctccc gcgcaattta atatttatgc tgacagtcca    1080
ctgacttata gtggtgagaa cgctaacttt atccggcgct taccctgctc ttctgggaac    1140
cctattggtc cagtcgtcgt cggcaaaact gttgaccgcg ctatcggttg gatgcctcaa    1200
tttgatcccg cctcttctta caatcctgat ttggctatgg actccttatc taaagccacg    1260
acgctaccgc ttcgcgcaaa attttcgccc ttctggtctg gtccagcttt attctctttc    1320
gcttcttgcg atcggaagaa tggaatttac gatgtctctt tcatgtccca atttccatct    1380
ttgtatttca gtgatgatga cacagcctct agatcccggt tctcttccta tcgcgccgtc    1440
aaagacagat ctttgctgaa ggacacagct aacttactgt atatctcgaa cttggccagt    1500
tcgcacgatc accgccttat tccagactcg aagaccatgg tgtacgttgg ggcttcaggt    1560
acgcacgcgg ataatcagcc atctgtcatc aagcctttac taaatgggtc acttccgggc    1620
gtctttaaac ctctctctgt gaagcagatt ggatgggagg tgactaatgg tactatttgc    1680
gacattgagt taccactcgc gacaggcaca ttttcttcg tctacagcga tgtcgatcaa    1740
gttcaggctg gtgactccga tcttgatgcc tcttcccgcc gcttctgctc ccaattggac    1800
atgcttgtca aattgacata cacaggtgga tccgtcgttg ctaaatgtaa cttcccaact    1860
aatctcgttt ggcggcacct cttttacgacc gtttctccat acttttcttc tattcatctg    1920
ctgaaaccac taatcgctaa taatttggag ttgtatgttc tattggctga aagttgcca    1980 gttcctgaag cgtccttcct cccttctgca gatatggtcg tcttctggag atcacagatt    2040
caacgttatc gaactttacg tgattctttt gctgtagttc cctcgattga ctctactctt    2100
agcttggaag atgatttaac tgtttctgtt ctgaattttg ttgatgtgac ttctctctca    2160
tctgtggaag atcaacatgc cctggctgcc ttttcagtaa ttacttcatt agggtctcag    2220
aaactgtcga ttcaccccta ttttgatagt taccgtactc agctgatcgg ataatcact    2280 ccccactctc gtaacgtatt ggataggctg gcgtacatac cgcgtgtgtt tccctctacc    2340
attgatgttc agcatcgcat catgtcgtca tctgaccctg agatcttcgg tttccgctct    2400
acctattgga ctcagctctc attcttttat gacaatgcat tgatgcagat ggatttcact    2460
gaagcgaaac attggcttga cttagggaca ggacctgaag ctaggccttt atctttcttg    2520
ccctccgatc ttcccgtcac cctgtgtgat actcgacctt tcatatttcc ttctggttgc    2580
tgggccacgt tcacagattt tcttagttac gattacctaa ccacaaatgt tattctctcg    2640
```

```
accggagctg atgttgtatc ttgcgttctc actttaggtg ctgcttgtgc cgacgcgaac    2700
ataacgcttc atgagggagt tcgccagata gttttcacaat gtgtggatgc caatgttaag    2760
acgctcttct tacagctcaa ttgtcctttg ccttctgccg gtgatgtgcc ccgtgacgtt    2820
ttggaactgg tgcagactaa ctcgacttac attttccatt cgttgggccg cattgaacct    2880
tttattcctt actctgctct tcttgagatc gtggaggact tatgcccggg tatcgttgtg    2940
gagattaaga cgatggatcc atctctttcg tggctcaatt acgctgtaca ttttaatgca    3000
tctgttcctt ccgatgatat agtgttggct atgcggttgt ctcacttctg tccctattc    3060 gtgtttcact tgaaccgtca ttcagctgat tttccagacg atgcgcgcgt aggtctcct    3120 tttacggttt tactgtccaa ttatgaggac acagctctt atgaggttac tttagataac    3180
gtcacgattg ctacaatcac tgctggatct cttgtgggct tttcatcggg tgtccaggtc    3240
gcttcaaaag atgatcaact cactttaacc ataaactctg ccagtcctgg aattttgtct    3300
attattcagg tgctcccggt gcgtgtctct cttggcagct gtgtgataga ggcccccagac    3360 ccttcactgt ccttgatttt cccggccaaa ctggacacat ctctatcggg cacagatctg    3420
gaattgttct tatctgattg gtatgatgtc gctttattct atattgatga agccaactct    3480
cgtttgttgc cggtgtcgga taccaagtac gaaatttaca gaaaagatca aactccaggt    3540
actaggacga ttaattatat cttcgatcgc tcagatgtct tcttcaaaat agtgttgtgt    3600
gacgtttctc atcaggagt tggccgattc atttatcgcg agctaccga gttaagttca    3660 cccgtgtggc ctgaagacgt tcgcaccttt ctatcgctac ctttcgactc tccaatggtc    3720
attatctctc ctgatggtcc tgtgaactac gatggtgcga ctgtgacgcc cccacgtct    3780 tggttgacag ttgacggtag tacatgcgtt gtcgatggtc ggccttcatt ctttgtgcct    3840
cccggtagat atggcctggt gagagtctag acgaccgcgg gcctccagta gaagggtgtt    3900
actcatc                                                              3907
```

<210> SEQ ID NO 6
<211> LENGTH: 2283
<212> TYPE: DNA
<213> ORGANISM: Artificial Sequence
<220> FEATURE:
<223> OTHER INFORMATION: Reoviridae

<400> SEQUENCE: 6

```
gcttttctcg acatggccta tctagccaca cctgtgctag gagtcggttc tcgcattacc      60
gccttagatc gtactattga tgctatcacg ttgaaacctc gaatcgacct ccaagatgtg     120
tatacgcttg atcccacact gacgttgcgt cagatagagt taatctcttc gggaacttca     180
atggacgata tcgctcgtgg actattgcac cgggactggc gtcgtcaatc caccattgtc     240
ttgcttcctt cccgtcgctc tctccttgag tatttactgt ctaacccttc ctcttgtcca     300
gatggtttag atcgctctcg actcaaagga tttcaaaagc gaccaaatga ttttcgtgtt     360
caggatttct tttcgccatt gattacggac actacgtcaa tcgctaccta ctctcgatgg     420
cttaatgctc atcctaccgt gtactctact acccataaag ttgccggcgc ccgagtgcgt     480
ctctttggac ccgctaaatt gtacatcctg tcgcctgatg ttcttcgtga ttatccatt     540 ttgaaatcca ctgatcgcat actcgttgtg cccacagctc gtgtgtatgt tggttgtttt     600
cccagcgctt ctactagtaa ttgtgtactc actgcacgtg agcgttggaa tgctcctgac     660
gttcatccag ttgtcaaagc aattcagtta gcatacgatc atcaatatcg tgtcaccgct     720
cgctatctct ctgatcctct tgtctcagct ctccttcttg gaactcggtc ggtcaagacg     780
```

```
ttgaaagtac agccgataga agctcgagcc gcacgatcag ttggcatccg cgtacaagcg     840
atgacacctc cccgtggcat taacacctca attattcaag tcgttgatct taggctacag     900
tgtcgtcatt ccctcatccc cactgaaagg ccattcccgt taacgtttgt cggcctccca     960
tcgtgtttgc ttcaacattt ggatttaaca ttatctgatg actgggtgcc cattcgtgat    1020
catacaggta tgtttgagat gtggtttatg attcttactc tcacttgtga taaaattctt    1080
gacggacggg ggagcgccgt ttttctcatt cccagctcta ctaatgcact gtcaattaac    1140
tatgtacagc tcacgtcgac cgcgtctcca cgtccccaat cgttggcagc taacgcatct    1200
ggacggatag attccattgg actgtgtatg cccaaaggat ctttcaagtc gaccatgatt    1260
aaatttctca ctggactaga aatttgcggc acgcgagtaa tgtacccgga cgtcgtgatg    1320
gacagtgatg acgtgggtga cgctttggat cctacttttg aaactgccct atatgacgca    1380
ttgatagctc ttgacccgcc ctttgacgtt gacaagttag ctagtcctac tgatttagtc    1440
aatcaggagt atgttgcatc ccacatgtac ccgacgttct tgaggcttgt caatgagttg    1500
ctgactccca aagcttcaga gttatactcg gagcgtagtg tcgaattccg atctctcact    1560
tacgcgcatg ccgattctga atttcttaac gcttgctgga ccgctcgttt gatgcgctgc    1620
tttatcaatt atcatgagga gcagaatatc ctgcttcgtc ctgggcgcgt tggtggtgta    1680
ctattccagg ttgcgctgag tcgctgttat aagatgttcg ctacttctac tcctgcttcc    1740
cctctgtcat tgttcctcaa gtcgttgttt gtccctgga ttgaatctgc cccactgtta    1800
gctagtctca cgccaaacga atcttctcgt gtgctagcat ggtatatccc ttcctcgtac    1860
tggagcgaca atggctggtg cacttgtgac actcatcgtc acgtcacctt ttctttcatt    1920
cgcggtcttc ctactgacct gtcggtgtta gatctatttg attggtctcg ctttcgtgcg    1980
actataaacg tagacacatc tctagtggag ttgggcgctg atatccgtgc agttaaagta    2040
tccgttcatt ggacatctca gaagcccact gtggacgttt ttgacaatcg tgcgcttttc    2100
actcccttcc agcactacca tttgagtctc cattgtaact gcgcgcccgg tcgcccgttc    2160
tttgcgaaga acatgaaact atatttgtcg acggttggag gcgagcactg acgggccatg    2220
gggcggtgac acccagggag ggtatgctgg taaccctggg ttagtcgtct tgagatactc    2280
atc                                                                  2283
```

<210> SEQ ID NO 7
<211> LENGTH: 2158
<212> TYPE: DNA
<213> ORGANISM: Artificial Sequence
<220> FEATURE:
<223> OTHER INFORMATION: Reoviridae

<400> SEQUENCE: 7

```
gcttttcag tgcctatctt tctcacaaca tgggtaacgc gacgtctgta gtacagaact      60
ttaacatcca aggtgatggc aatcactttg caccttcagc cgaaaccaca tcatccgctg     120
taccctccct ttcattaaat cctggtttgc tcaatcccgg cggcaaagct tggactttga     180
ttgacgcgtc tctcaatgca tcggatccat cttccctgcg gttaatgact tcggctgatc     240
tgtctacgct gtcccaatct gctgttggta attctactgg attcctacca acttcgggca     300
tgtatgctct gaccactaag gagacattaa gtgttgtgac ggatcatgct atagcacagt     360
ttgaaaaatt gcagatggcc tgtgagttag atcgtgatta tttggatgct cgcggcgtat     420
cacctgaatc tgttaacatc cataactata tagtgtatgt cgactgtttc gtgggcgttt     480
```

```
ctgctcgcca agccgcatca aacttccaac aacgtgtgcc agttataacc aaatccagga      540
tgactcaatt catgacatcc gcacagaata ttctacaggt acttggtccc tgggagcgtg      600
atattcgtga attgcttact atcatacccc cttctactac cgctggcaag ttatcatgtg      660
acatgaggtc agtagttagt ttcgtcgata gtcagctatc agatacgagt ttgtgccgcc      720
tctacccaga atgtgctgca gcagccgtgg ctagaaggaa tggtggaata cgttggaagc      780
aggctgatag tgatgaagcc ccttctcttg ctactaatga catagctgct tcaacgatgg      840
gagcccttgc taatactact cctctctcgg agaagtctaa ttccggcgaa gagtccatgc      900
gtctagtgaa tgatgtgggc gtagacatta tgagctcccg aggccccatt agttcctccg      960
tgtggtcccg tactgttgaa cctaaatctt acaatattag gacacttcgt gtggaagaag     1020
cgttatggct gcgtgagagt caggctactg ctggtttcga cgtctcatac actctgcctg     1080
atcaaactac ccagaagcat ttttggctgc agaaaggctc tactgtgatc aatcttgagc     1140
aaactggtag tatgatgttc gaagtaaacg tgtctggcaa ggattacaag aaaggctctt     1200
tcgatcctga taatcataag ttggttcttc ttgtgatgca atccaagata cccttttgaat     1260 cttggacagg ggcgtcccaa attgatggta ttgcacaagt agccgaggtg acagtgcacg     1320
cagctgatag ttctacgcct agccgtaaga tcataggggα gacgtcacta tcctacttgt     1380
ttgagagaga aacggttacc accgccaaca ctgaggttaa cacttacctc ctatgcacgt     1440
ggcagcttga tgacgcacaa agtaatgcg acaatgcgtg gcccgacgca tgggatgcaa     1500
tcactacctt gacgtcatta acttcgggaa ctgtgacgat taaagggaca tccgtagatt     1560
ccgtcactcc ggttgattta gttggagctt atacacctga agccctttcc gcagcccttc     1620
caaacgatgc cggccttata ctcgcggata agctacgaa gctggctaat gccattaaga     1680
aggaagatga ttctgttatt gatgaatcgt caccttttag tactccgatt caaggtgtgt     1740
tagcggttca gcaactggac accgttggta cacgaggtgt acgaacgatt cagcccccag     1800
cgtttctaaa acgtgttgcc ctcgagctt tgcatatgtt tctgggtgat ccccattcta     1860
tcctcaagca aactacgcct gtgctaaaag atcctgaagt ctggactgga ttcattcaag     1920
gcgtgcgaga tggcatccgt actaaatcat tgtccgcggg agtgagatct gtttataata     1980
acgtcaccgc aacacagtcc gttcaaacgt ggaagcaggg gtttctgact aaaatacaga     2040
cgttgttcaa accatcgtga ggtgctaagg cctctctccg cggcgggtcg gtgggcacgt     2100
cgtggtgatg ctgaatgcac ggggggggtga cgccctctgg attggcacgt tactcatc      2158
```

<210> SEQ ID NO 8
<211> LENGTH: 1996
<212> TYPE: DNA
<213> ORGANISM: Artificial Sequence
<220> FEATURE:
<223> OTHER INFORMATION: Reoviridae

<400> SEQUENCE: 8

```
gcttttgag tcctagcgtg gatcatggcg tcaaccaagt ggggagacaa gccgatgtcg       60
ctctcaatgt ctcacgatgg atcatctatc cgcagtgctg cctcacagtt tttgtcggtc      120
cctctgtctc actcaacgcc tatcccacct caacggaaga ccgtgctgtt gaaatttatg      180
attggcgatg atctggttac cgttcagggt gccctcgccc cgtttgatga gtattggtac      240
gataaccaac ctctgctagc tcaggctgtt gagatgcttg cttctgaaga tcgtttacgt      300
caattcgagc attatgagaa atttctactc aagaaaggtc atcagatagc tgagattatg      360
aacaggttac gcctcttttt cacagacgtt cttaaagtta agatggaagc tgaggcttta      420
```

-continued

```
cctgctttag ctcaatatct aatggttgga accttagagg ctgtttctac tgctcattca        480
cctgatgctt gtgttccagt tacctcaaag gtcgtgacta agcagcagac tattgctaaa        540
tctcctggcc gtctcgatga ggaggaatac aacgttattc gatcgcgttt cctgacgcac        600 gaggttttg atctgacgtc cgacttaccc ggagtgcaac cttcatgga tatgtactac          660 gctaccgtcc ctcgcgccga ttcgacagga tggtgtgtgt accgtcgcaa gggcttactc        720
attcactctc ctgatgagca attctcagat ctgactatct tctctacacg tcttacggct        780
tcgcatgagt tgcagctcgt ggctggagat gtcgtcgtgg cgtgctttga tctcatggac        840
gtttctgaca tcgcgccatc tcatcatgca tcagtgcaag aggaacgtac tctcgggacc        900
agtaaatatt cgaatataac ggctaacgat catcctctgg tattcttctc acccagtgcg        960
cttcgttggg cgattgacca tgcttgcacc gattccttag tttctactcg aaatatccgt        1020
gtttgtgttg gtatcgatcc cctggtaact cgatggaccc gagacggggt acaagaggcc       1080
gctatcctca tggatgataa actaccatca gcaggccgtg cacgtatggc tttgcggaca       1140
ttgcttctcg ctagacgttc accaatgcca tctttcttac tgggggcctt aaagcagtcg       1200
ggcggtcagt tactggagca ctatcgatgt gacgcggcta acagatacgg atctcctacc       1260
gtacccatgt ctcatccacc accgtgttca agtgtcctg aactgaaaga acaaattacc        1320
aaactctcgt cctcgcctac acccaaaatc gactctacca ctggccccgc tgcactgttg       1380
tcaaaatttt ctgacctcca gcgtgctaat agggaactgt cactgaaact ggtcgatatg       1440
caacctgctc gggaggacca cctgctgtct tatctcaatg aacacgtgtg cgtaaatgct       1500
agagatcatg agaagggtct gctctctcgc tgcaacgtat ctaatgaatc gatctcctct       1560
atccttgacc agcgtatgaa gaatcgggaa cggtttgaga ctcggctgcg gcatgaggcc       1620
agtgctgaat gggaacctcg tgtggaagcg ctaaaccaag agttggccaa agctcgtgtg       1680
gaacagcagg acatgatgac tcagtctcta cagtacttaa acgagcgtga cgaattactc       1740
cacgaagtgg acgagctcaa acgtgaactg accaccctgc gcgccgctaa tgtgcgcttg       1800
aacgctgaca atcatcggat gagccgtgca actcgtgttg gagacgcttt cgtcagcgac       1860
atcgagcctc tgccctctgg catacctggt gaatcgaaac catctatgga agaattggta       1920
gatgatctgt gagctttgac ttgtgactcg acttctctct gattccatgt acccacggcg       1980
gactcggtta ttcatc                                                       1996
```

<210> SEQ ID NO 9
<211> LENGTH: 1645
<212> TYPE: DNA
<213> ORGANISM: Artificial Sequence
<220> FEATURE:
<223> OTHER INFORMATION: Reoviridae

<400> SEQUENCE: 9

```
gcttttcaa tcccttgtgt cgatgttccc gtatgtcatc tggttcatgt aacggtgcaa         60
cttctatttt tggtaacgtt cactgtcagg cagcgcaaaa ctcggcgggt ggtgatcttc        120
aagcgacttc ctctcttgtt gcttattggc cctacttggc tgcgggcggt ggtctgctcg       180
ttgttattat tataattgtt ggcgctgttt gttgttgcaa ggctaaggtt aaagcggacg       240
cagcccgaaa cgttttctac cgagagctgt tcgcacttaa ttcgggtaaa agtgatgcag       300
gacctccgat ttaccaggtt tagtgtacga cgatttgagt tttcaccttt cgtcttagag       360
gagtgcacta ctccatcttt cacgactata actaataccg atccggctct ctactttaac       420
```

```
attgagtttc cgtcaagtca tcgtctctcc cccttcattc cagaactgtt gtctcagcct    480
tgtaccgttc acgtttcatt gattcggaga ttcgctctct gtgcaaccct atctagtatt    540
tgtgaatacg actgtgcgct actgccatcc atcaacgcta ttacgacgat ccctacacca    600
ggtgcgtcat catctctgat tgttcattgg gatggaaggc ttaactcagt cacagcgaag    660
agaggtcgtg gggctgatac tctcattgac ttcgaacgtg actataaatc ctggcgattt    720
gacggaactg cgtgagcgcg tctcggcgtt agaatcggcc aatgcgtcgt tgaatgagat    780
cataaaaggc gtgttagatc agttggtaga tttggcacag aagttgggca atgcggcggg    840
tgctgtagtt gacctacgag gagagctgaa ctcattaact gccagcgtcc aaactatcca    900
atcttctttg ggatcactca cggacagtat atcggatctt tctagccaag tgactactaa    960
cgcctcttcg cccacgaatc tgaggagtat ggtggcgggt cttatagctg atgtgactaa   1020
tcttaaacgt gacgtatcga atcagggtct tcaaatgacg agtctcgagc agcgtgtaac   1080
tagtttggaa tctggtactg gatctattcc cacatttgct gctcccctta aattagatgg   1140
cgggattgtt tcactcgatc tggacccctta cttttgttct gtggaccata atctcacgtc   1200
gtattccgca agcgctctgc taatgaattt tcagtggctt gttcgaggtg agggagggtc   1260
gtctgactca ttcgatatga atgtgacagc tcatagccac ggccagagga cagatttttat  1320
gatgtctacc actcagtcgt taactgttac tggaaattct gtcactctag tctttgatct   1380
taatgcgctt atttctccac cctccgacta ttctcgcttg ataccatgtc atggtttcca   1440
acaagcgacg tttcccgtgg acctttcgtt taagcgagac gacgtcacgc actcatatca   1500
ggtgtatggt tcgtacacaa ctcctcgcat tttcaagata actttctccc ctggcaatcc   1560
agtacctgcg gtcatacgtt tcataaccgt gcgtacgggc atcgatactt aaggtgtggc   1620
gccgtacggg gattggttat tcatc                                         1645
```

<210> SEQ ID NO 10
<211> LENGTH: 1324
<212> TYPE: DNA
<213> ORGANISM: Artificial Sequence
<220> FEATURE:
<223> OTHER INFORMATION: Reoviridae

<400> SEQUENCE: 10

```
gcttttctc ccacgatggc gcgtgccgta tacgacttct tttctacgcc tttcgggaat     60
cgtggtctag caacgaatcg tactcaacta tcatcactac taacaagctc gaattcccca    120
tggcaacgat ttctatcttc aatgactcca ttgacggcgc caggtattgt ctcaacacct    180
gaagcaccct atccgggctc actgatgtat caagagtcca tgcttcacag tgccactgtc    240
cctggagtac ttggtaatcg tgatgcttgg cgtacgttta atgtcttcgg gctttcatgg    300
actgacgaag gactgtcagg actggtggct gctcaagatc ctcctcccgc cgccccgtat    360
cagccagcct ctgctcagtg gtcagatctc ctcaactacc ccagatgggc gaacagacgt    420
cgtgagttac aatcaaaata cccgcttctg cttcgatcca cgctgctttc tgccatgcga    480
gctggtcctg ttcttttatgt tgagacgtgg ccgaatatga tctcaggacg gctagccgac    540
tggttcatgt cccaatatgg caacaatttc gttgacatgt gtgccaggtt gacacagtct    600
tgtttgaaca tgcctgtcga acctgatggg aattacgatc agcagatgcg tgctttgatc    660
agtttgtggc tcctttcgta cattgggta gtcaatcaga ctaataccat cagcggcttc     720
tacttctcct cgaagactcg gggtcaagcg ttagacagtt ggaccttatt ttacaccaca    780
aacaccaatc gtgtccaaat tacccagagg catttcgctt acgtgtgtgc acggtcccct    840
```

```
gattggaacg tggataaatc gtggatcgct gcggcgaatt tgaccgctat catcatggcc    900
tgtcgtcaac cgccaatgtt tgccaaccaa ggcgttatca accaagcgca gaaccggcct    960
ggcttttcca tgaatggagg gacgcccgtt cacgagctca acttactgac taccgcgcag   1020
gaatgcatta ggcagtgggt ggtagctggt ctggtgtcag cggcgaaggg gcaaacatta   1080
acacaagagg ctaatgactt ttcggccctc atccaggcag atctaggaca aatcaaggcg   1140
caggatgatg ctctgtacaa tcagcagcca ggatacgcaa ggagaataaa acccttcgtt   1200
aacggtgact ggacaccagg catgaccgcg caagctctgg ccgttctagc cacttttacc   1260
gcctaggcgt agggtcgtac gctgcccgag tccagccctc cggcagcacg tgggtgtact   1320
catc                                                                1324
```

<210> SEQ ID NO 11
<211> LENGTH: 1202
<212> TYPE: DNA
<213> ORGANISM: Artificial Sequence
<220> FEATURE:
<223> OTHER INFORMATION: Reoviridae

<400> SEQUENCE: 11

```
gcttttgag tccttagcgt gcaagccgca atggaggtac gtgtgccaaa ctttcactcg     60
ttcgttgaag gaataacatc cagttactta cagactcctg cttgttggaa tgcacaaaca   120
gcctgggaca ctgtgacctt tcatgtccct gatgtcatta gagtcggtaa cgcgtactgt   180
tgttctcagt gctgcggtgt actttactac ggaactctgc catccgacgg gaattacttc   240
cctcatcaca aatgtcatca gcaacagttt aggactgata ccccgctact gcgatacgta   300
aggatcggca gaacgactga gcatttgctg gatcagtatg ccgtcgcttt ggagtctatc   360
gccgaacact atgatgagat cagccaacgt atggttgatg agcctgagaa tgatgaagtt   420 acgcccctg acatcgtaac gcgcaccgag tctatcagaa gtgacaaggc agtggacccg   480
gacttttgga cctatccact tgagcgacgc tctgatgact ctcgccggga tatcgcctca   540
gcatgctgga aaatgattga tgcgtcctca cgtagtctga ccctccccaa ctgtcttgtt   600
tctccatctg tgcattcacg ttccgtcttt ggtcaaatgc aaacgaccac caccatatac   660
gatgttgctg cgtctggaaa ggcagttaag ttttctccga tggttgctac cctcgctcaa   720
cgcgatgctg ggcctgtgac gctcgcaaac gctgatccag ctgacggcgt atactcgttt   780
tggacatcac actttgcctt ttcgccactc attggtggag tcgggattac agggcaatat   840
gctcgcgagt cataccacca cgtgggtcat ccggtaattg ggagcggtaa gaaggcgtcg   900
cactacagaa atctgttcat ggaagcgtgg cgtgggtggt cgaagtccgc ttttgcgtgt   960
gctacaggta tggagcctgc tgaatgtgag tcccgtttga gaggacacgc ccgcaccatg  1020
ctcggacggt ctctaccaaa tgtctgtgat gatgatgtcg ctcaacagtc tggtgctgtg  1080
ctagcatctc tgcagaagac taccaaattc actgtggtgg agtgtggttg gtaagtgcct  1140
ccgggtcaaa atgcacatag gctcccacct atgtgacggt tagcgggact cgcctattca  1200
tc                                                                 1202
```

<210> SEQ ID NO 12
<211> LENGTH: 1192
<212> TYPE: DNA
<213> ORGANISM: Artificial Sequence
<220> FEATURE:
<223> OTHER INFORMATION: Reoviridae -continued

```
<400> SEQUENCE: 12
gctttttgag tccttgtgca gccatggaca acaccgtgcg tgttggagtt tcccgcaaca     60
catccggcgc agctggtcag actgttttta gaaactacta cctactacga tgcaacatct    120
cagctgacgg tcgtaatgca acaaaagctg tgcaatccca ctttccattc ctttctcgtg    180
ctgtccgatg cttatctcct ctagctgctc attgtgccga taggactctc cgtcgtgaca    240
acgtgaagca gattctcact cgtgaactac catttccatc ggatctaatc aattacgcgc    300
accacgtgaa ttcatcctcg cttactactt ctcagggtgt tgaggcagcc cgtctggtgg    360
ctcaagttta tggagagcaa ctgtcatttg accacatcta ccccactggt tctgcaacat    420
actgccctgg agcgattgcg aatgcgattt cccgtatcat ggctggcttc gtcccccacg    480
aaggcgacaa ctttacccca gatggtgcca tcgattatct cgctgcagat ctggtcgcgt    540
acaagtttgt gcttccttac atgctagaca ttgtggacgg gcgtccgcag attgttctcc    600
catctcacac tgttgaggaa atgctgtcca acacgagctt gcttaattca attgacgctt    660
catttggtat tgaatctaag agcgatcaac gcatgacccg tgacgcggct gaaatgagtt    720
ctcgttcact taatgagctt gaggatcacg agcagagggg tcgaatgcct tggaaaatca    780
tgacggcgat gttcgcggcg caactgaagg tggagctgga tgccctagct gatgagcggg    840
ttgagtctca ggctaatgct cacgtgacat cttttgggtc tcgtctgttc aaccagatgt    900
ctgcttttgt cccgattgat cgtgagttga tggagctggc tctactcatt aaagaacaag    960
gtttcgcaat gaatccaggg caagttgcat ctaaatggtc gctgatacga cgatctggtc   1020
ccactcgccc actctcaggc gcgcgccttg agatcagaaa tggtaactgg acgattcgtg   1080
aaggtgacca gacacttctg tctgtctctc cagctaggat ggcgtaaacg ggacccatgg   1140
tgcgggtgag gggccgccac accctctgcc gcgacctgga ctcttattca tc           1192
```

AVIAN REOVIRIDAE AND VACCINES THEREOF

This application is the National Stage of Int'l App'l No. PCT/US2009/048860, filed Jun. 26, 2009, which claims priority of U.S. Ser. No. 61/076,102, filed Jun. 26, 2008.

Throughout this application, various references or publications are cited. Disclosures of these references or publications in their entireties are hereby incorporated by reference into this application in order to more fully describe the state of the art to which this invention pertains.

FIELD OF THE INVENTION

This invention relates to novel unique strains of avian reoviridae that were isolated from severe cases of Runting Stunting Syndrome. The present invention also relates to the isolation and uses of novel unique avian reoviridae, diagnostic assays using nucleotide or amino acid specific components of such viruses, such as the sequence encoding Sigma C capsid protein and to vaccines that protect birds from diseases caused by such viruses.

BACKGROUND OF THE INVENTION

Reoviridae such as inter alia reovirus, which replicate in the cytoplasm, are nonenveloped with an icosahedral symmetry and a double-shelled capsid. The viral genome consists of 10 double-stranded RNA (dsRNA) segments, which can be separated into three size classes: L (large), M (medium), and S (small). Proteins encoded by the genome are also separated into three sizes. The specific genome segments responsible for protein coding have been identified for the S1133 strain of avian reovirus.

Avian reoviruses are members of the orthoreovirus genus in the Reoviridae family. Ubiquitous in commercial poultry, they can be differentiated by antigenic configuration, pathotype, relative pathogenicity, growth in cell culture, embryonated chicken eggs sensitivity to trypsin, and host and tissue specificity.

Classic reoviruses have been isolated from a variety of tissues in chickens affected by assorted disease conditions, including viral arthritis/tenosynovitis, stunting syndrome, respiratory disease, enteric disease, immunosuppression, and malabsorption syndrome. They have frequently been found in chickens that were clinically normal. The nature of the disease that occurs following reovirus infection is very much dependent upon host age, immune status, virus pathotype, and route of exposure. Reoviruses have also been isolated from turkeys, ducks, geese, pigeons, pheasants, parrots, and other exotic avian species.

In young meat-type chickens, economic losses related to reovirus infections are frequently associated with increased mortality, viral arthritis/tenosynovitis, and a general lack of performance including diminished weight gains, poor feed conversions, uneven growth rates, and reduced marketability of affected birds.

Avian Malabsorption Syndrome

Avian Malabsorption Syndrome (MAS) also known as Runting Stunting Syndrome (RSS) is a disease of growing poultry, especially chickens or turkeys, with meat-type or broilers being affected most commonly. This disease has been reported in the Netherlands as Runting and Stunting Syndrome (RSS) but also under different names for example infectious stunting syndrome, enteritis, pale bird syndrome, helicopter disease, infectious proventriculitis, brittle bone disease and femoral head necrosis.

Kouwenhoven et al. (Avian Pathology 17:879-892, (1988)) further defined MAS by five criteria: 1) growth impairment up to 3 weeks after infection of one-day old chicks; 2) excretion of yellow orange mucoid to wet droppings; 3) increased plasma alkaline phosphatase (ALP) activity; 4) decreased plasma carotenoid concentration (PCC); and 5) macroscopically widened epiphyseal growth plates of the proximal tibia. The condition has been further characterized by stunted growth, poor feathering, maldigested feed, lack of skin pigmentation, enteritis, pancreatic atrophy, proventriculitis, thymic and bursal atrophy and bone changes.

The transmission of the disease is effected by oral inoculation of intestinal homogenates from affected chicks into one-day-old broilers. In that experiment, it was demonstrated that low plasma carotenoid levels and elevated ALP activities are suitable tools for the diagnosis of MAS or RSS. In further experiments, MAS was transmitted by oral inoculation of liver homogenates from affected chicks into one-day-old broilers. Despite years of research, the etiology of MAS has not yet been fully established, and the condition is still a major economic problem for the poultry industry. It is believed that viruses are responsible, but bacteria or other microorganisms have not been excluded as causal agents.

Viruses that have been found in birds with outbreaks of MAS or RSS possibly include reoviruses, rotaviruses, parvoviruses, entero-like viruses and a toga-like virus (McNulty and McFerran, 1993, and Pantin-Jackwood MJ- and et al., AVIAN DISEASES 52:235-244, 2008). McNulty (World Poultry 14:57-58 (1998); and Pantin-Jackwood MJ (2008)), summarized the state of art on MAS, and have postulated that identification of the viral causative agent is unknown and recommends control by careful management of production sites.

SUMMARY OF THE INVENTION

The present invention provides newly isolated unique avian reoviridae serotypes, designated AVS-A, AVS-B, and AVS-A/B, which have been deposited with the American Type Culture Collection ("ATCC" 10801 University Boulevard, Manassas, Va. 20110-2209 USA) under Budapest Treaty on Jun. 26, 2008 and have accession numbers PTA-9301, PTA-9302, and PTA-9297 respectively. Also, nucleotide sequences encoding antigenic epitopes of these novel serotypes, corresponding to the inner core proteins, e.g., σA proteins of the novel avian reoviridae serotypes have been characterized. AVS-A and AVS-B reoviridae serotypes comprise an ORF sequence encoding an inner core protein (σA proteins) as set forth in one or more of the following nucleotide sequences: SEQ ID NO.1 and 2, respectively, or a sequence having at least 85%, 90%, 93%, 95%, or 97% homology with a nucleotide sequence as set forth in SEQ ID NO: 1 and/or SEQ ID NO: 2. Preferably, novel isolated avian reoviridae serotypes of the invention comprise a nucleotide sequence capable of hybridizing under stringent conditions with one or more nucleotide sequences selected from the group consisting of SEQ ID NO: 1 and SEQ ID NO: 2.

The present invention also relates to newly characterized nucleotide sequences of reoviridae genome, comprising more precisely the sequence of the genomic L1 segment (3958 base pairs) with a predicted open reading frame between nucleotides 21-3882 encoding the λA protein (SEQ ID NO: 3), the sequence of the genomic L2 segment (3829 base pairs) with a predicted open reading frame between nucleotides 14-3793 encoding the λB protein (SEQ ID NO: 4), the sequence of the genomic L3 segment (3907 base pairs) with a predicted open reading frame between nucleotides 13 to 3870 encoding the λC protein (SEQ ID NO: 5), the sequence of the genomic M1 segment (2283 base pairs) with a predicted open reading frame between nucleotides 13 to 2211 encoding the μA protein (SEQ ID NO: 6), the sequence of the genomic M2 segment (2158 base pairs) with a predicted open reading frame between nucleotides 30 to 2060 encoding the μB protein (SEQ ID NO: 7), the sequence of the genomic M3 segment (1996 base pairs) with a predicted open reading frame between nucleotides 25 to 1932 encoding the μNS protein (SEQ ID NO: 8), the sequence of the genomic S1 segment (1645 base pairs) with a predicted open reading frame between nucleotides 632 to 1612 encoding the σC protein (SEQ ID NO: 9), the sequence of the genomic S2 segment (1324 base pairs) with a predicted open reading frame between nucleotides 16 to 1266 encoding the GA protein (SEQ ID NO: 10), the sequence of the genomic S3 segment (1202 base pairs) with a predicted open reading frame between nucleotides 31 to 1134 encoding the GB protein (SEQ ID NO: 11), and the sequence of the genomic S4 segment (1192 base pairs) with a predicted open reading frame between nucleotides 24 to 1127 encoding the σNS protein (SEQ ID NO: 12). Accordingly, the present invention also provides nucleotide sequences from novel unique reoviridae as set forth in SEQ ID NOs: 3-12, as well as portions thereof encoding for the above listed reoviral proteins, sequences having at least 85%, 90%, 93%, 95%, or 97% homology with nucleotide sequences as set forth in SEQ ID NOs: 3-12, and/or sequences capable of hybridizing under stringent conditions with one or more nucleotide sequences selected from the group consisting of SEQ ID NOs: 3-12.

The present invention further relates to a composition comprising novel isolated unique avian reoviridae serotypes comprising nucleotide sequences, portions thereof as set forth in SEQ ID NOs: 3-12, or a sequence having at least 85%, 90%, 93%, 95%, or 97% homology with nucleotide sequences as set forth in SEQ ID NOs: 3-12, or a sequence capable of hybridizing under stringent conditions with one or more nucleotide sequences selected from the group consisting of SEQ ID NOs: 3-12.

In another embodiment, a vaccine is provided for use in the protection of poultry against disease conditions resulting from avian reovirus infections, comprising the reoviridae isolates or a part of the nucleotide sequence of reoviridae isolates disclosed herein, and a pharmaceutically acceptable carrier.

The invention also relates to a vaccine comprising antigenic materials derived from the novel isolated unique avian reoviridae serotypes wherein said materials comprise amino acid sequences encoded by nucleotide sequences as set forth in SEQ ID NOs: 1-12, or by a sequence having at least 85%, 90%, 93%, 95%, or 97% homology with nucleotide sequences as set forth in SEQ ID NOs: 1-12, or by a sequence capable of hybridizing under stringent conditions with one or more nucleotide sequences selected from the group consisting of SEQ ID NOs: 1-12.

The present invention also provides antiserum that is induced in an animal by the unique avian reoviridae serotypes disclosed herein. In another embodiment, there is also provided antibodies that bind to the unique avian reoviridae isolates disclosed herein.

The present invention further provides a method of eliciting an immune response in poultry comprising administering a composition comprising the novel unique avian reoviridae serotypes disclosed herein or amino acid sequence thereof encoded by nucleotide sequences as set forth in SEQ ID NOs: 1-12, or by a sequence having at least 85%, 90%, 93%, 95%, or 97% homology with nucleotide sequences as set forth in SEQ ID NOs: 1-12, or by a sequence capable of hybridizing under stringent conditions with one or more nucleotide sequences selected from the group consisting of SEQ ID NOs: 1-12.

The present invention also provides a method of protecting poultry against disease conditions resulting from an avian reovirus infection, comprising the step of administering the vaccine disclosed herein to the poultry.

The present invention also provides a method of detecting the presence of novel avian reoviridae isolates in poultry, comprising the steps of: obtaining a sample from the poultry; contacting the sample with antibodies or probes that bind to the avian reoviridae isolates disclosed herein; and detecting binding of the antibodies or probes to the sample, wherein detected binding would indicate the presence of reoviridae isolates of the present invention in the poultry.

The present invention also relates to a method of quantifying novel avian reoviridae isolates in poultry comprising the steps of contacting a sample from poultry with an antibody which binds to the novel reoviridae isolates or the amino acid sequence encoded by nucleotide sequences as set forth in SEQ ID NOs: 1-12, or by a sequence having at least 85%, 90%, 93%, 95%, or 97% homology with nucleotide sequences as set forth in SEQ ID NOs: 1-12, or by a sequence capable of hybridizing under stringent conditions with one or more nucleotide sequences selected from the group consisting of SEQ ID NOs: 1-12, and measuring the amount of binding of the antibody to a component of the sample.

The present invention also provides a container comprising at least one dose of the vaccine composition as disclosed herein. The present invention further provides a kit comprising the container and an instruction manual, including information for the administration of at least one dose of the vaccine to poultry for lessening the severity of the MAS or RSS and sequelae including immune suppression.

The present invention further provides diagnostic kits comprising probes that are capable of hybridizing under stringent conditions with nucleotide sequences as disclosed, herein or comprising antibodies that are capable of binding with reoviridae serotypes of the invention.

BRIEF DESCRIPTION OF THE DRAWINGS

FIG. 1 shows the nucleotide sequence encoding σA protein (inner core protein) of reoviridae serotype AVS-A of the present invention.

FIG. 2 shows the nucleotide sequence encoding σA protein (inner core protein) of reoviridae serotype AVS-B of the present invention.

FIG. 4 shows the sequence of the genomic L1 segment (3958 base pairs) with a predicted open reading frame between nucleotides 21 to 3882 encoding the λA protein (SEQ ID NO: 3).

FIG. 5 shows the sequence of the genomic L2 segment (3829 base pairs) with a predicted open reading frame between nucleotides 14 to 3793 encoding the λB protein (SEQ ID NO: 4).

FIG. 6 shows the sequence of the genomic L3 segment (3907 base pairs) with a predicted open reading frame between nucleotides 13 to 3870 encoding the λC protein (SEQ ID NO: 5).

FIG. 7 shows the sequence of the genomic M1 segment (2283 base pairs) with a predicted open reading frame between nucleotides 13 to 2211 encoding the µA protein (SEQ ID NO: 6).

FIG. 8 shows the sequence of the genomic M2 segment (2158 base pairs) with a predicted open reading frame between nucleotides 30 to 2060 encoding the µB protein (SEQ ID NO: 7).

FIG. 9 shows the sequence of the genomic M3 segment (1996 base pairs) with a predicted open reading frame between nucleotides 25 to 1932 encoding the µNS protein (SEQ ID NO: 8).

FIG. 10 shows the sequence of the genomic S1 segment (1645 base pairs) with a predicted open reading frame between nucleotides 632 to 1612 encoding the σC protein (SEQ ID NO: 9).

FIG. 11 shows the sequence of the genomic S2 segment (1324 base pairs) with a predicted open reading frame between nucleotides 16 to 1266 encoding the σA protein (SEQ ID NO: 10).

FIG. 12 shows the sequence of the genomic S3 segment (1202 base pairs) with a predicted open reading frame between nucleotides 31 to 1134 encoding the σB protein (SEQ ID NO: 11).

FIG. 13 shows the sequence of the genomic S4 segment (1192 base pairs) with a predicted open reading frame between nucleotides 24 to 1127 encoding the σNS protein (SEQ ID NO: 12).

DETAILED DESCRIPTION OF THE INVENTION

Figure 3:
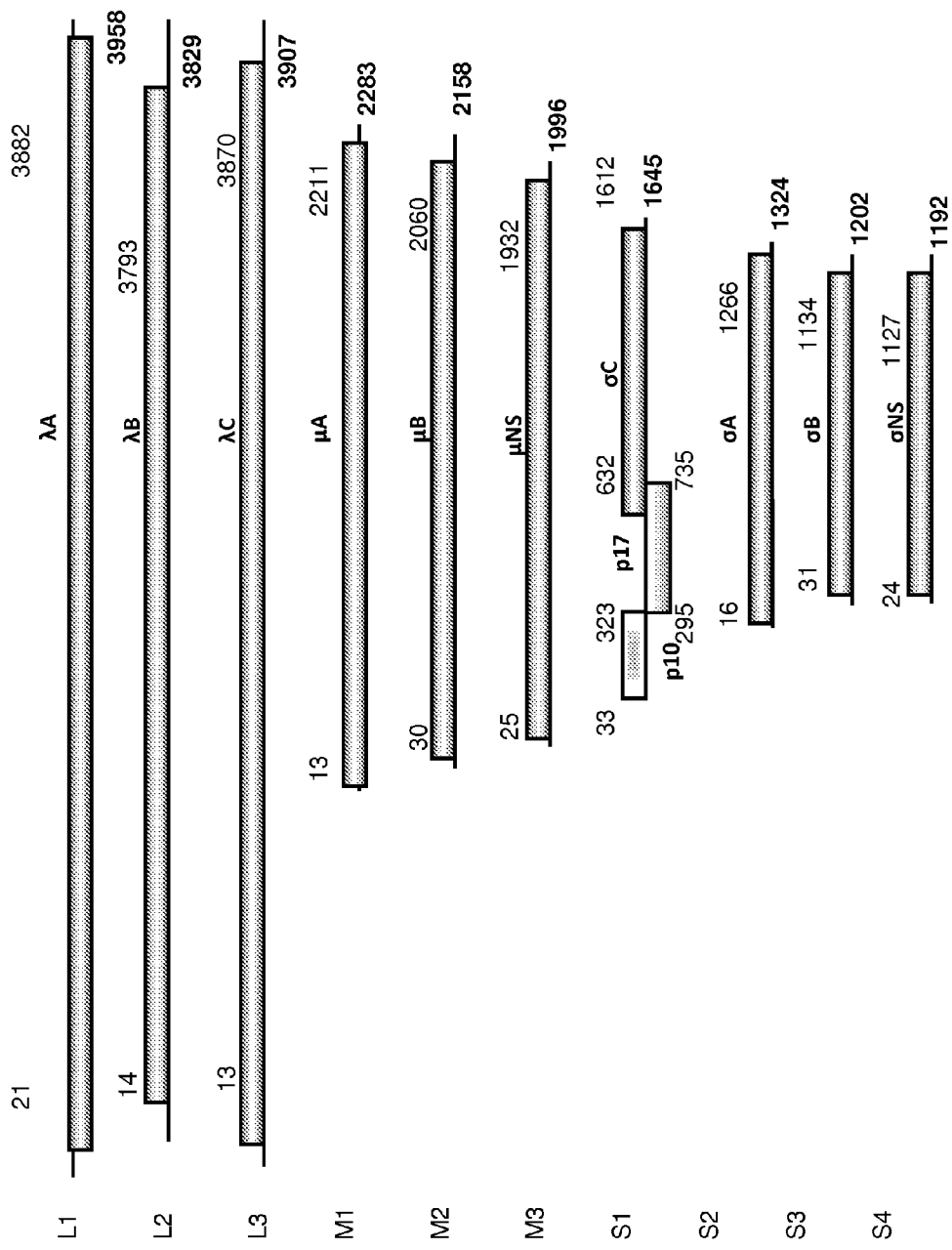
FIG. 3 shows the genome segment designation (L1-L3, M1-M3, S1-S4; on the left), lengths of each genome segment (expressed in base pair; numbers on the right), the location and size of the predicted open reading frames and the protein names are indicated (shaded boxes).
Figure 14:
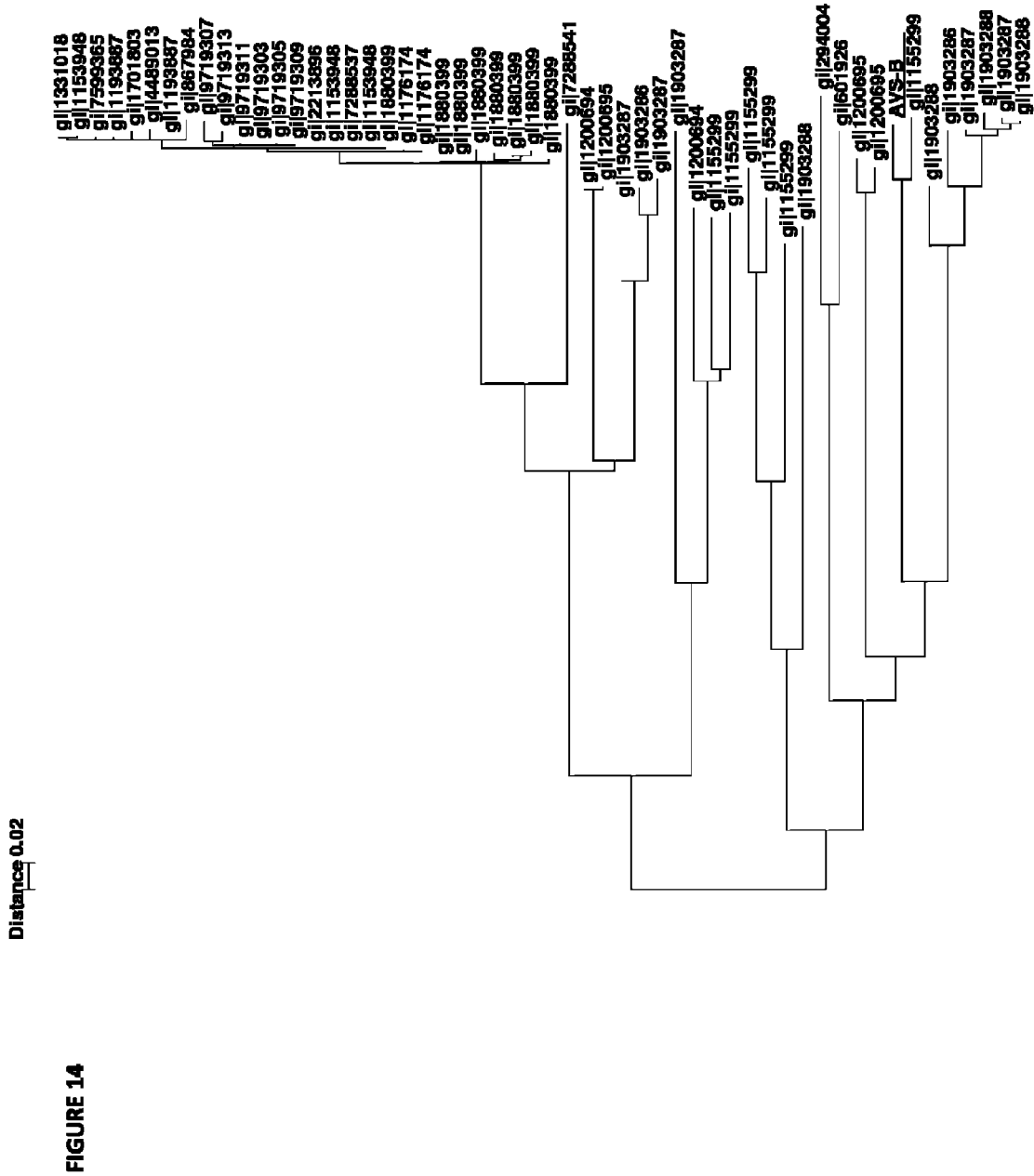
FIG. 14 shows the phylogenic relationships among avian reovirus. The novel serotypes isolated by the inventors from clinical cases of Runting and Stunting Syndrome are underlined.

Avian reoviridae display displays considerable antigenic heterogeneity and the emergence of new antigenic and pathogenic classes of avian reoviridae may have important implications for the use of reoviridae vaccines in poultry. The present specification now identifies a novel antigenic class of avian reoviridae. Furthermore, it is demonstrated that avian reoviridae isolates belonging to this novel antigenic class are able to induce pronounced disease conditions associated with Avian Malabsorption Syndrome (MAS) also known as Runting and Stunting Syndrome (RSS).

In one embodiment, the present invention provides a new antigenic class of avian reoviridae as a causative agent of a variety of disease conditions in affected poultry, i.e., RSS disease, including enteritis. In another embodiment, the present invention provides a vaccine which effectively affords protection in poultry against disease caused by avian reoviridae of the new antigenic class. In yet another embodiment, the present invention provides a vaccine which effectively affords protection in poultry against variety of disease conditions in affected poultry, i.e., RSS disease, including enteritis.

These newly isolated unique avian reoviridae serotypes, designated AVS-A, AVS-B, and AVS-A/B, have been deposited with the American Type Culture Collection ("ATCC" 10801 University Boulevard, Manassas, Va. 20110-2209 USA) under Budapest Treaty on Jun. 26, 2008 and have accession numbers PTA-9301, PTA-9302, and PTA-9297 respectively. The reoviridae serotype AVS-A/B presents antigenic epitopes common to serotypes AVS-A and AVS-B, and thus corresponds to a natural reassortment thereof.

The present invention thus relates to compositions comprising the newly isolated unique avian reoviridae serotypes as described above. Compositions of the invention may further comprise a pharmaceutically acceptable carrier, adjuvant, or diluents. The composition may comprise an isolated reovirus, a live reovirus that is attenuated, or an isolated reovirus that is inactivated. Compositions may comprise at least $10^2$ titration units of the reoviridae isolates.

The invention also relates to nucleotide sequences encoding antigenic epitopes of the novel serotypes, corresponding to the inner core proteins of the novel reoviridae serotypes have been characterized. AVS-A and AVS-B reoviridae serotypes comprise an ORF sequence encoding an inner core protein as set forth in one or more of the following nucleotide sequences: SEQ ID NOs: 1 and 2, or a sequence wising having at least 85%, 90%, 93%, 95%, or 97% homology with a nucleotide sequence as set forth in SEQ ID NO: 1 and/or SEQ ID NO: 2. Preferably, novel isolated avian reoviridae serotypes of the invention comprise a nucleotide sequence capable of hybridizing under stringent conditions with one or more nucleotide sequences selected from the group consisting of SEQ ID NO: 1 and SEQ ID NO: 2.

The present invention also relates to novel isolated nucleotide sequences of reoviridae genome, comprising more precisely the sequence of the genomic L1 segment (3958 base pairs) with a predicted open reading frame between nucleotides 21 to 3882 encoding the inner core λA protein (SEQ ID NO: 3), the sequence of the genomic L2 segment (3829 base pairs) with a predicted open reading frame between nucleotides 14 to 3793 encoding the inner core λB protein (SEQ ID NO: 4), the sequence of the genomic L3 segment (3907 base pairs) with a predicted open reading frame between nucleotides 13 to 3870 encoding the λC protein (SEQ ID NO: 5), the sequence of the genomic M1 segment (2283 base pairs) with a predicted open reading frame between nucleotides 13 to 2211 encoding the inner core µA protein (SEQ ID NO: 6), the sequence of the genomic M2 segment (2158 base pairs) with a predicted open reading frame between nucleotides 30 to 2060 encoding the outer capsid protein, µB protein (SEQ ID NO: 7), the sequence of the genomic M3 segment (1996 base pairs) with a predicted open reading frame between nucleotides 25 to 1932 encoding the non structural protein, µNS protein (SEQ ID NO: 8), the sequence of the genomic S1 segment (1645 base pairs) with a predicted open reading frame between nucleotides 632 to 1612 encoding the outer capsid sigma C protein, σC protein (SEQ ID NO: 9), the sequence of the genomic S2 segment (1324 base pairs) with a predicted open reading frame between nucleotides 16 to 1266 encoding the inner core protein, σA protein (SEQ ID NO: 10), the sequence of the genomic S3 segment (1202 base pairs) with a predicted open reading frame between nucleotides 31 to 1134 encoding the outer capsid protein or σB protein (SEQ ID NO: 11), and the sequence of the genomic S4 segment (1192 base pairs) with a predicted open reading frame between nucleotides 24 to 1127 encoding the σNS protein (SEQ ID NO: 12). Accordingly, the present invention also provides nucleotide sequences from novel unique reoviridae as set forth in SEQ ID NOs: 3-12, as well as portions thereof encoding reoviridae peptides or portions thereof, sequences having at least 85%, 90%, 93%, 95%, or 97% homology with nucleotide sequences as set forth in SEQ ID NOs: 3-12, and/or sequences capable of hybridizing under stringent conditions with one or more nucleotide sequences selected from the group consisting of SEQ ID NOs: 3-12.

The present invention also relates to nucleotide sequences or portions thereof encoding antigenic epitopes of the avian reoviridae serotypes as set forth in SEQ ID NOs: 3-12, or a sequence having at least 85%, 90%, 93%, 95%, or 97% homology with nucleotide sequences as set forth in SEQ ID NOs: 3-12, or a sequence capable of hybridizing under stringent conditions with one or more nucleotide sequences selected from the group consisting of SEQ ID NOs: 3-12.

A most preferred nucleotide sequence according to the present invention comprises a nucleotide sequence as set forth in SEQ ID NO: 9 encoding the outer capsid protein, σC protein of reoviridae, or nucleotide sequence as set forth in SEQ ID NO: 11 encoding the outer capsid σB protein, and/or the nucleotide sequence as set forth in SEQ ID NO: 7 encoding the outer capsid μB protein. According to a preferred embodiment, antigenic epitopes are encoded by nucleotide sequences chosen among SEQ ID NOs: 7, 9, or 11, or a sequence having at least 85%, 90%, 93%, 95%, or 97% homology with nucleotide sequences as set forth in SEQ ID NOs: 7, 9, or 11, and/or a sequence capable of hybridizing under stringent conditions with one or more nucleotide sequences selected from the group consisting of SEQ ID NOs: 7, 9, or 11. According to a most preferred embodiment, antigenic epitopes are encoded by a nucleotide sequence as set forth in SEQ ID NO: 9, or a sequence having at least 85%, 90%, 93%, 95%, or 97% homology with a nucleotide sequence as set forth in SEQ ID NO: 9, and/or a sequence capable of hybridizing under stringent conditions with SEQ ID NO: 9.

The present invention further relates to a composition comprising novel isolated unique avian reoviridae serotypes comprising antigenic amino acid sequences encoded by nucleotide sequences, or portions thereof as set forth in SEQ ID NOs: 1-12, or a sequence having at least 85%, 90%, 93%, 95%, or 97% homology with nucleotide sequences as set forth in SEQ ID NOs: 1-12, or a sequence capable of hybridizing under stringent conditions with one or more nucleotide sequences selected from the group consisting of SEQ ID NOs: 1-12.

In general, appropriate antiserum raised against the live reoviridae isolates disclosed herein can be prepared by inoculating 3 to 4 weeks old chickens subcutaneously, intramuscularly or intravenously with a live virus strain having an infectious titre between $10^2$-$10^9$ TC ID$_{50}$/animal; more preferably between $10^3$-$10^6$ TC D$_{50}$/animal. Blood can be collected 3 to 4 weeks after infection, preferably 4 weeks after infection. Chickens may also be reinfected with the same live virus strain 3 to 4 weeks after the first infection with approximately the same dose as used in the first infection. Blood is collected between 2 and 4 weeks after the second infection.

Appropriate antiserum can also be raised against inactivated avian reoviridae strains disclosed herein by inoculating 3 to 4 weeks old chickens subcutaneously or intramuscularly with the inactivated virus preparation. The infectious titre of the preparation before inactivation may be between $10^7$-$10^{11}$ TC ID$_{50}$/animal; more preferably between $10^8$-$10^{10}$ TC ID$_{50}$/animal. Blood can be collected 4 to 6 weeks after inoculation, preferably 5 weeks after inoculation. Chickens may also be re-inoculated with the same inactivated virus preparation 3 to 6 weeks after the first inoculation. Blood is collected between 3 and 5 weeks after the second inoculation.

The present invention also provides a vaccine for use in the protection of poultry against disease conditions resulting from an avian reoviridae infection, such as RSS disease including enteric disease conditions, comprising an avian reoviridae according to the invention and a pharmaceutically acceptable carrier or diluent.

The reoviridae isolates or a part of its genome according to the present invention can be incorporated into the vaccine as a live attenuated or inactivated virus or as subunit vaccines or as part of a recombinant vaccine. The property of the avian reoviridae isolates to induce RSS-associated disease conditions as described herein are significantly reduced or completely absent if the avian reoviridae isolate is in a live attenuated or inactivated form or as a subunit vaccine or as part of a recombinant vaccine.

The vaccine may comprise antigenic materials derived from the novel isolated unique avian reoviridae serotypes wherein said materials comprise amino acid sequences which are encoded by nucleotide sequences as set forth in SEQ ID NOs: 1-12, portions thereof, or by a sequence having at least 85%, 90%, 93%, 95%, or 97% homology with nucleotide sequences as set forth in SEQ ID NOs: 1-12, or by a sequence capable of hybridizing under stringent conditions with one or more nucleotide sequences selected from the group consisting of SEQ ID NOs: 1-12.

Attenuation of an avian reoviridae isolate according to the invention can be achieved by methods well known in the art for this purpose, such as disclosed in Gouvea et al. (Virology 126:240-247, (1983)). Briefly, after the isolation of the virus from a target animal, a virus suspension is inoculated onto primary (avian) cell cultures, such as chicken embryo liver cells (CEL), Chicken kidney cells (CK), or mammalian cell lines such as the VERO cell line, BGM-70 cell line or avian cell line such as QT-35, QM-7, LMH, or other susceptible cell culture. If the isolate is not able to produce cytopathic effect (CPE), then the virus is passaged repeatedly (e.g. 3-10 times) until CPE is observed. As soon as CPE is visible, cells and cell culture fluids are collected, frozen and thawed, clarified by centrifugation and the supernatant containing the avian reoviridae isolate is aliquoted and stored at −20° C. This process may be repeated (e.g. 10-100 times) to further attenuate the virus.

In one embodiment, a vaccine according to the present invention can be prepared by conventional methods such as, for example, commonly used for the commercially available live- and inactivated reoviridae vaccines. For example, the preparation of veterinary vaccine compositions is described in "Vaccines for Veterinary Applications" (ed.: Peters, A. R. et al., Butterworth-Heinemann Ltd, 1993).

In one embodiment, the vaccine according to the present invention containing live attenuated virus can be prepared and marketed in the form of a (frozen) suspension or in a lyophilised form. The vaccine additionally may contain a pharmaceutically acceptable carrier or diluent customarily used for such compositions. Carriers include stabilisers, preservatives and buffers. Suitable stabilisers are, for example, SPGA, carbohydrates (such as sorbitol, mannitol, starch, sucrose, dextran, glutamate or glucose), proteins (such as dried milk serum, albumin or casein) or degradation products thereof. Suitable buffers are for example alkali metal phosphates. Suitable preservatives are thimerosal, merthiolate and gentamicin. Diluents include water, aqueous buffer (such as buffered saline), alcohols and polyols (such as glycerol).

In another embodiment, the live vaccines according to the present invention may contain an adjuvant. Examples of suitable compounds and compositions with adjuvant activity are generally known in the art for the preparation of vaccines.

Although administration by injection, e.g., intramuscular, subcutaneous of the live vaccine according to the present invention is possible. The live vaccine is preferably administered by the inexpensive mass application techniques commonly used for avian reovirus vaccination. These techniques include drinking water and spray vaccination. Alternative methods for administration of the live vaccine include in ovo, eye drop and beak dipping administration.

In another embodiment, the present invention provides a vaccine against enteric disease conditions, such as those observed with RSS, comprising the reoviridae isolates disclosed herein in an inactivated form. The major advantage of an inactivated vaccine is the elevated levels of protective antibodies of long duration that can be obtained. This property makes such an inactivated vaccine in particular suited for vaccination of chicken and turkey breeder stocks.

The aim of inactivation of the viruses harvested after the propagation step is to eliminate reproduction and infectiousness of the viruses. In general, this can be achieved by chemical or physical means. Chemical inactivation can be effected by treating the viruses with, for example, enzymes, formaldehyde, beta-propiolactone, ethylene-imine or a derivative thereof. If necessary, the inactivating compound is neutralized afterwards. Material inactivated with formaldehyde can, for example, be neutralized with thiosulphate. Physical inactivation can preferably be carried out by subjecting the viruses to energy-rich radiation, such as UV light or γ-rays. If desired, after treatment the pH can be adjusted to a value of about 7.

A vaccine containing the inactivated avian reoviridae isolates disclosed herein can, for example, comprise one or more of the above-mentioned pharmaceutically acceptable carriers or diluents suited for this purpose. Preferably, an inactivated vaccine according to the present invention comprises one or more compounds with adjuvant activity. Suitable compounds or compositions for this purpose include aluminium hydroxide, -phosphate or -oxide, oil-in-water or water-in-oil emulsion based on, for example, a mineral oil, such as Bayol F® or Marcol 52® or a vegetable oil such as vitamin E acetate, and saponins. In general, inactivated vaccines are usually administered parenterally, e.g., intramuscularly or subcutaneously.

The vaccine according to the present invention comprises an effective dosage of the reoviridae isolates disclosed herein as the active component, i.e., an amount of immunizing avian reoviridae material that will induce immunity in the vaccinated birds or their progeny against challenge by a virulent virus. Immunity is defined herein as the induction of a significantly higher level of protection in a population of birds after vaccination compared to an unvaccinated group. Typical doses and schedule for vaccination are generally known in the art.

The reoviridae vaccines according to the present invention may be used effectively in poultry, i.e., chickens as well as other poultry such as turkeys, guinea fowl and quail. Chickens include broilers, reproduction stock and laying stock. Turkeys include meat-type birds and breeder stock.

The present invention also provides combination vaccines comprising, in addition to the avian reoviridae of the present invention, one or more vaccine components of other pathogens infectious to poultry. In general, such other pathogens infectious to poultry are antigenically distinct from the unique avian reoviridae of the present invention. In one embodiment, the vaccine components in the combination vaccine are live attenuated or inactivated forms of the pathogens infectious to poultry. In another embodiment, the present invention provides a combination vaccine wherein all of the vaccine components are in an inactivated form.

In another embodiment, a vaccine is provided for use in the protection of poultry against disease conditions resulting from an avian reoviridae infection, comprising the reoviridae isolates disclosed herein, and a pharmaceutically acceptable carrier. In general, the vaccine may comprise the avian reoviridae in a live attenuated or inactivated form. The vaccine may further comprise an adjuvant.

In another embodiment, the vaccine may be a combination vaccine and comprises one or more vaccine components against a second pathogen infectious to poultry. The combination vaccine comprises, in addition to the novel reoviridae serotypes, one or more of an astrovirus, other classical avian reovirus, an infectious bronchitis virus (IBV), Newcastle disease virus (NDV), infectious bursal disease virus (IBDV), fowl adenovirus (FAV), EDS virus (type III adenovirus) and turkey rhinotracheitis virus (TRTV). Preferably, the combination vaccine comprises astrovirus as a second pathogen.

The invention thus also provides a vaccine for use in the protection of poultry against disease conditions and particularly syndromes of MAS or nephritis resulting from an avian reoviridae and astrovirus co-infection, comprising the reoviridae disclosed herein, an astrovirus and a pharmaceutical acceptable carrier.

In general, the vaccine may comprise the reoviridae isolates and astrovirus and in live attenuated or inactivated forms. The vaccine may further comprise an adjuvant.

The present invention also provides subunit vaccine comprising the reoviridae isolates of the present invention. Genes from the reoviridae isolates disclosed herein producing protective proteins against the disease could be cloned into expression vectors or carriers generally known in the art. Expression of these protective proteins could then be produced as subunit vaccines according to standard procedures well-known in the art.

The present invention also provides recombinant vaccines comprising the reoviridae isolates of the present invention. Genes from the reoviridae isolates disclosed herein producing protective proteins against disease could be cloned into live or inactivated vectors or other carriers generally known in the art for expression of these proteins as vaccines. In addition, these viruses themselves could be used as live attenuated vaccines (vectors) to carry genes producing protective proteins from other agents allowing for protection against the vector as well as the inserted gene. More precisely, the invention relates to nucleotide sequences: SEQ ID NOs: 1-12, or a sequence comprising having at least 85%, 90%, 93%, 95%, or 97% homology with a nucleotide sequence as set forth in SEQ ID NOs: 1-12. Preferably, novel isolated avian reoviridae serotypes of the invention comprise a nucleotide sequence capable of hybridizing under stringent conditions with one or more nucleotide sequences selected from the group consisting of SEQ ID NOs: 1-12.

The present invention also provides antiserum that is induced in an animal by the reoviridae isolates and an astrovirus disclosed herein. The present invention also provides antibodies that bind to the reoviridae isolates and astrovirus disclosed herein. In one embodiment, the antibodies are monoclonal antibodies, polyclonal antibodies, chimeric antibodies, or single chain antibodies, bispecific antibodies, synthetic antibodies, antibodies fragment such as Fab, F(ab)2, Fv, or scFv fragments, or chemically modified derivatives thereof.

Monoclonal antibodies can be prepared, for example, by the techniques which are well known to a skilled person in the art. Such techniques involve the fusion of mouse myeloma cells to spleen cells derived from immunized mammals. Furthermore, antibodies, or fragments thereof, can be obtained by using methods which are described, for example, in Harlow and Lane, Antibodies, A Laboratory Manual, CSH Press, Cold Spring Harbor, 1988. Useful antibodies, or their corresponding immunoglobulin chain(s), can be further modified using conventional techniques known in the art, for example by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art (see, e.g., Sambrook, Molecular Cloning: A Laboratory Manual, Cold Spring Harbor Laboratory (1989) N.Y.).

The present invention also provides a method of protecting poultry against disease conditions, particularly severe RSS and sequelae resulting from an avian reoviridae and astrovirus co-infection, comprising the step of administering the vaccine disclosed herein to the poultry. Examples of poultry include, but are not limited to, chickens, turkeys, guinea fowl, and quail.

The present invention also provides a method of detecting the presence of unique avian reoviridae in poultry, comprising the steps of: obtaining a sample from the poultry; contacting the sample with antibodies or probes that bind to the reoviridae disclosed herein; and detecting binding of the antibodies or probes to the sample, wherein detected binding would indicate the presence of the novel avian unique reoviridae of the present invention in the poultry. In general, the sample is prepared from intestine, liver, or feces of the poultry. Examples of poultry include, but are not limited to, chickens, turkeys, guinea fowl, and quail.

The method of detecting and/or method of quantifying novel avian reoviridae isolates in poultry may comprise the steps of contacting a sample from poultry with an antibody which binds to the novel reoviridae isolates or the amino acid sequence encoded by nucleotide sequences as set forth in SEQ ID NOs: 1-12, or by a sequence having at least 85%, 90%, 93%, 95%, or 97% homology with nucleotide sequences as set forth in SEQ ID NOs: 1-12, or by a sequence capable of hybridizing under stringent conditions with one or more nucleotide sequences selected from the group consisting of SEQ ID NOs: 1-12, and measuring the amount of binding of the antibody to a component of the sample.

By way of example, the amount of novel reoviridae isolates in poultry may be measured using the ELISA assays. In practice, standards and samples to be tested are incubated in a in microtiter wells pre-coated with antibody that captures the reovirus. The standards and samples are diluted in a buffer containing detergent for 1 hour at room temperature prior to loading the microtiter wells. The captured reoviridae particles are then detected, for example, with biotinylated second antibody that binds to the reoviridae which is then detected, for example, by using a streptavidin-peroxidase conjugate and colored substrate. The concentration of the reoviridae particles is then determined using a standard curve prepared from known amounts of the reoviridae particles. ELISA techniques are well known to those of ordinary skill in the art.

The present invention further provides a diagnostic kit comprising antibodies or probes that bind to the reoviridae disclosed herein, means for detecting antibodies or probes, thereby allowing following the presence of avian reoviridae and the level of infection of poultry.

The present invention also relates to a novel propagation cell line which is derived from original LMH cell lines (ATCC accession number CRL 2117), which has been adapted as non-collagen dependent cell line and to grow on plastic plates. The novel propagation cell line LMH-KJ has been deposited with the American Type Culture Collection ("ATCC" 10801 University Boulevard, Manassas, Va. 20110-2209 USA) under Budapest Treaty on Jun. 26, 2008, and has accession number PTA-9299.

The present invention further relates to a method of propagating novel isolated reoviridae serotypes consisting in infecting the non-collagen dependent cell lines LMH-KJ, culturing the cells under same growing conditions as that of cells LMH (ATCC accession number CRL 2117) with gentamicin, and harvesting reoviridae when CPE is visible.

The age of the animals receiving a live or inactivated vaccine according to the invention is the same as that of the animals receiving the presently commercially available live- or inactivated avian reoviridae vaccines. For example, broilers may be vaccinated directly from one-day-old onwards with the live attenuated vaccine according to the invention. Vaccination of parent stock, such as broiler breeders, can be done with a live attenuated or inactivated vaccine according to the invention or combinations of both. The advantages of this type of immunization program include the immediate protection of one-day-old progeny provided by maternally derived antibodies vertically transmitted to the young birds. A typical breeder vaccination program includes the vaccination of the breeders at 6-weeks of age with a live attenuated vaccine, followed by a vaccination between 14-18 weeks of age with an inactivated vaccine. Alternatively, the live vaccination may be followed by two vaccinations with inactivated vaccines on 10-12 weeks and 16-18 weeks of age.

The present invention finally provides a container comprising at least one dose of the vaccine as described herein, and a kit comprising such container with an instruction manual, including information for the administration of at least one dose of the vaccine to poultry for lessening the severity of the RSS and sequalae.

The invention being generally described, will be more readily understood by reference to the following examples which are included merely for purposes of illustration of certain aspects and embodiments of the present invention, and are not intended to limit the invention.

EXAMPLES

Example 1

Isolation of Reoviridae

The reoviridae isolates disclosed herein were isolated from several diseased chickens, from Delmarva USA. The reoviridae isolates were cultivated in an adapted hepatocellular carcinoma cell line (CH-SAH, which is alternatively called the LMH cell line). The original LMH cell line was obtained from the American Type Culture Collection (ATCC), accession number ATCC CRL 2117.

Example 2

PCR and Sequencing

Double stranded RNA was isolated from reoviridae isolates serotypes AVS-A, AVS-B and AVS-A/B using the Quiagen RNA purification kit. Multiple RT-PCRs were conducted according to published reovirus procedures. Using the procedures of Xie et al. (AVIAN DISEASES 41:654-660 (1997). Amplification of the unique avian reoviridae RNA using the Reverse Transcriptase-Polymerase Chain Reaction (RT-PCR) to amplify the sigma C protein gene, an outer capsid protein gene on segment S1, no PCR products were detected for either serotypes AVS-A, AVS-B, or AVS-A/B, while known avian reovirus strains S1133, 2408 and SS412 amplified the expected 523 bp product.

RT-PCR was conducted following the procedures of Zhang et al. (Arch Virol (2006) 151:1525-1538). Detection and identification of avian, duck, and goose reoviruses by RT-PCR: goose and duck reoviruses are part of the same genogroup in the genus Orthoreovirus) to amplify the inner core protein gene, sigma A gene on the S2 segment. PCR products of approximately 600 bp were amplified for serotypes A and B, as well as S1133, 2408, and SS412.

These RT-PCR primers for the reoviridae sigma A, inner core protein gene and the reoviridae sigma C outer capsid protein gene were used to identify the causative viral agents as the RSSV. The reoviridae outer capsid primers do not amplify genes from these reoviridae isolates while the reoviridae inner core primers do. In addition, the rotavirus outer capsid primers did amplify the avian rotavirus but not the RSSV (Table 1).

TABLE 1

Differential identification of viruses involved in RSS using RT-PCR

| Avian Virus | Strain Name | Reovirus Inner Core RT-PCR for σA | Reovirus Outer Capsid RT-PCR for σC | Rotavirus Outer Capsid RT-PCR |
|---|---|---|---|---|
| Reovirus | S1133 | Positive | Positive | Negative |
| Reovirus | 2408 | Positive | Positive | Negative |
| Reovirus | SS412 | Positive | Positive | Negative |
| Rotavirus | Ch2/5 | Negative | Negative | Positive |
| Reoviridae | AVS-A | Positive | Negative | Negative |
| Reoviridae | AVS-B | Positive | Negative | Negative |
| Reoviridae | AVS-A/B | Positive | Negative | Negative |
| Astrovirus | AVS-1 | Negative | Negative | Negative |
| IBDV | Standard | Negative | Negative | Negative |
| IBDV | Variant E | Negative | Negative | Negative |

Example 3

RT-PCR and Sequencing

Using the procedures of Zhang et al ((Arch Virol (2006) 151:1525-1538) to amplify the inner core protein gene, sigma A gene on the S2 segment, RT-PCR products of approximately 600 bp were amplified for AVS-A, AVS-B, AVS-A/B, S1133, 2408, and SS412. These RT-PCR products were purified and sequenced using these primers. The sequences of the RT-PCR products for AVS-A and AVS-B were 100% similar to one another. When compared to strains S1133 and SS412, the sequences were highly conserved. When the sequences were blasted in PudMed, the reoviridae were 90% similar to avian reovirus accessions for ARV17 and 99G. Avian reovirus strain S1133 was 100% similar to 99G and SS412 was 93.7% similar to OS161.

Example 4

Efficacy of inactivated RSSV Vaccine

The efficacy of an inactivated RSSV vaccine was evaluated in progeny chicks of vaccinated breeder hens. The RSSV vaccine consists of reoviruses (designated AVS-A, AVS-B) and an astrovirus (designated AVS-1) that were inactivated using 0.2% formalin (final concentration) and is adjuvanted with an oil based adjuvant. Groups 1 and 2 comprised of specific pathogen free chickens were vaccinated at 32 weeks of age with 0.5 ml of the vaccine subcutaneously in the back of the neck. Group 2 was revaccinated with 1.0 ml of the same vaccine at 4 weeks post 1st vaccination. The other group of the chickens (Group 1) was not revaccinated. The hens were bled right before the 1st vaccination and at 4 and 8 weeks post the 1st vaccination. Starting from four weeks after the 2nd vaccination, eggs were collected from the vaccinated hens and set in an incubator for hatching. After hatching, progeny chicks at day of age were challenged with 0.5 ml of AVS-A. Day of age specific pathogen free chicks were used as challenge controls (Group 3). The chicks that were challenged were necropsied for gross lesions associated with reovirus such as extended ceca with gaseous/yellow contents, pale intestines and distended, watery, gas-filled intestines.

After challenge with AVS-A, 80% (16/20) of the non-vaccinated, challenge controls developed gross lesions associated with reovirus (Table 2). For the progeny chicks from the hens vaccinated once (Group 1), only 21% (3/14) of chicks were protected against AVS-A. For the progeny chicks from the hens vaccinated twice (Group 2), 56% (10/18) of chicks were protected against AVS-A. This result suggests that vaccinating hens twice with the inactivated RSSV vaccine gives adequate protection in progeny chicks against reovirus.

In summary, the RSSV vaccine provided adequate efficacy against AVS-A in the progeny chicks from the hens vaccinated with the vaccine twice.

TABLE 2

Treatment groups and protection against challenge with AVS-A

| Group # | Treatment Group | # of hens | 1st vaccination (0.5 ml, 32 weeks of age) | 2nd vaccination (1.0 ml, 36 weeks of age) | Protection of progeny chicks, #protected/ #total (% protection) |
|---|---|---|---|---|---|
| 1 | RSSV vaccine (once) | 15 | Yes | No | 3/14 (21%) |
| 2 | RSSV vaccine (twice) | 15 | Yes | Yes | 10/18 (56%) |
| 3 | Non-vaccinated, challenge controls | 15 | N/A[1] | N/A | 4/20 (20%) |

N/A[1] = not applicable

Example 5

The Genomic Constellation of the Avian Orthoreovirus Strain AVS-B

The genomic RNA was extracted by the TRIzol method. Preliminary sequence information was obtained by gene specific RT-PCR amplification of fragments of each genome segment. A short oligonucleotide was ligated to the 3' ends of the genomic RNA, and then its complementary primers were used in combination with gene specific primers to determine the 5' and 3' ends of the genomic segments. Nucleotide sequences were determined by the dideoxy chain termination method.

The full-length genome (23,494 bp) of strain AVS-B was determined by the primer walking sequencing strategy. The length of untranslated regions ranged 12 nt to 30 nt at the 5' end, and 30 nt to 98 nt at the 3' end. The most 5' and 3' end sequences were conserved' in all genome segments (5' end, GCUUUU(U). 3' end, UCAUC). The L1 genome segment of AVS-B strain was most closely related to strain 918 (91% identity), while the L3 genome segment shared the highest nucleotide identity with strains 1017-1 and R2 (89%). Only two L2 genome segments of chicken avian orthoreovirus have been published so far (strains 138 and 176); AVS-B strain was more closely related to strain 138 (91% nt identity). Comparison of the M1, M2, and M3 genome segments revealed moderate to high sequence identities to other avian orthoreovirus strains, the most closely related isolates being 138 (M1, 90% identity), 601G (M2, 85% identity) and OS161 (M3, 88% identity). The S1 genome segment was found to be tricistronic with partially overlapping open reading frames (ORFs); the position of the 3 ORFs (p10, p17 and σC) was similar to that seen in other chicken avian orthoreovirus strains. The σC coding region shared low nucleotide identity to the majority of strains (30%-70%), except for GA 40973/2005, (93%) isolated from a similar case of RSS in the USA. With regard to the S2, S3 and S4 genome segments, AVS-B strain shared the highest nucleotide identity to 138 (S2, 93%; S3, 92%), and to recent US chicken avian orthoreovirus strains (up to 93%).

While the availability sequence information on avian orthoreovirus allowed gaining insight into the overall structure of avian orthoreovirus strains, this is the first to report on a full-length avian orthoreovirus genome sequence. The length of the AVS-B strain genome fell in the size range predicted based on full-length cognate genome segment sequences available for a handful of reference avian orthoreovirus strains. The majority of genes of AVS-B strain shared significant degrees of sequence conservation with related genes of prototype avian orthoreovirus strains (>85%). However, the S1 segment of the genome represented an exception. This genome segment shared only <67% nucleotide identity with corresponding genome segment of other avian orthoreovirus strains. On the other hand, the σC protein encoding region of the S1 genome segment was closely related to another US avian orthoreovirus strain isolated also from RSS. The low number of avian orthoreovirus gene sequences and the lack of absolute sequence identities with related strains did not permit to identify the possible parental strains of this novel strain. Nonetheless, there seems to be convincing evidence that accumulation of point mutations and reassortment of cognate genome segments played key role in the origin and evolution of the AVS-B strain.

What is claimed is:

1. A vaccine comprising a peptide encoded by SEQ ID NO: 1 or 2 and an adjuvant selected from aluminum hydroxide, aluminum phosphate, aluminum oxide, an oil-in-water or a water-in-oil emulsion.

2. The vaccine according to claim 1, wherein said oil is a mineral oil, a vegetable oil, vitamin E acetate or a saponin.

3. An inactivated avian reoviridae produced by contacting an avian reoviridae deposited at the ATCC under accession number PTA-9301, PTA-9302 or PTA-9297 with formaldehyde, beta-propriolactone or ethylene-imine and inactivating said avian reoviridae.

4. A vaccine comprising the inactivated reoviridae of claim 3 and a pharmaceutically acceptable carrier or diluent.

5. The vaccine of claim 4 further comprising an adjuvant.

6. The vaccine according to claim 5, wherein said adjuvant is aluminum hydroxide, aluminum phosphate, aluminum oxide, an oil-in-water or water-in-oil emulsion.

7. The vaccine according to claim 6, wherein said oil is a mineral oil, a vegetable oil, vitamin E acetate or a saponin.

8. The vaccine of claim 4, wherein the vaccine further comprises one or more vaccine components against a second pathogen infectious to poultry.

9. A kit for poultry vaccination comprising a container comprising a vaccine according to claim 4 and an instruction manual, the instruction manual including information for the administration of at least one dose of said vaccine to poultry for lessening the severity of MAS, RSS or sequelae.

10. An attenuated avian reoviridae produced by attenuation of an avian reoviridae deposited at the ATCC under accession number PTA-9301, PTA-9302 or PTA-9297, said attenuation comprising inoculating a primary cell culture with an avian reoviridae deposited at the ATCC under accession number PTA-9301, PTA-9302 or PTA-9297, or passaging said avian reoviridae on said cell culture until a cytopathic effect is obtained, and subsequent freezing, thawing and isolation of said attenuated reoviridae.

11. A vaccine comprising the attenuated reoviridae of claim 10 and a pharmaceutically acceptable carrier or diluent.

12. The vaccine according to claim 11 further comprising an adjuvant.

13. The vaccine according to claim 12, wherein said adjuvant is aluminum hydroxide, aluminum phosphate, aluminum oxide, an oil-in-water or water-in-oil emulsion.

14. The vaccine according to claim 13, wherein said oil is a mineral oil, a vegetable oil, vitamin E acetate or a saponin.

15. The vaccine according to claim 14, wherein said oil is a mineral oil, a vegetable oil, vitamin E acetate or a saponin.

16. The vaccine according to claim 14, wherein said oil is a mineral oil, a vegetable oil, vitamin E acetate or a saponin.

17. The vaccine according to claim 11, wherein the vaccine further comprises one or more vaccine components against a second pathogen infectious to poultry.

18. A kit for poultry vaccination comprising a container comprising a vaccine according to claim 11 and an instruction manual, the instruction manual including information for the administration of at least one dose of said vaccine to poultry for lessening the severity of MAS, RSS or sequelae.

* * * * *